United States Patent
Grate et al.

(10) Patent No.: US 6,606,567 B2
(45) Date of Patent: *Aug. 12, 2003

(54) METHODS FOR CHARACTERIZING, CLASSIFYING, AND IDENTIFYING UNKNOWNS IN SAMPLES

(75) Inventors: Jay W. Grate, West Richland, WA (US); Barry M. Wise, Manson, WA (US)

(73) Assignees: Battelle Memorial Institute, Richland, WA (US); Eigenvector Research, Inc., Manson, WA (US)

(*) Notice: Subject to any disclaimer, the term of this patent is extended or adjusted under 35 U.S.C. 154(b) by 118 days.

This patent is subject to a terminal disclaimer.

(21) Appl. No.: 09/797,162

(22) Filed: Mar. 1, 2001

(65) Prior Publication Data

US 2001/0029774 A1 Oct. 18, 2001

Related U.S. Application Data

(63) Continuation-in-part of application No. 09/372,641, filed on Aug. 10, 1999, now Pat. No. 6,408,250.

(51) Int. Cl.$^7$ .............................................. B06E 19/00
(52) U.S. Cl. ........................................... 702/22; 702/90
(58) Field of Search .............................. 702/22–24, 27, 702/90; 73/23.2, 23.21, 23.35, 23.36

(56) References Cited

U.S. PATENT DOCUMENTS

| | | | |
|---|---|---|---|
| 5,243,539 A | * | 9/1993 | Holt et al. .................... 702/30 |
| 5,450,193 A | * | 9/1995 | Carlsen et al. ............... 356/301 |
| 5,469,369 A | * | 11/1995 | Rose-Pehrsson et al. ..... 702/27 |
| 5,571,401 A | * | 11/1996 | Lewis et al. ................. 205/787 |
| 5,918,263 A | * | 6/1999 | Thundat ..................... 73/35.16 |
| 6,093,308 A | * | 7/2000 | Lewis et al. ................. 205/787 |
| 6,244,096 B1 | * | 6/2001 | Lewis et al. .................. 73/23.2 |
| 6,319,724 B1 | * | 11/2001 | Lewis et al. ................. 436/149 |
| 6,408,250 B1 | * | 6/2002 | Grate et al. ................... 702/30 |

OTHER PUBLICATIONS

"Hydrogen Bonding", MH Abraham et al., p. 213–228, 1991.

"Solubility Factors for 240 Solutes and 207 Stationary Phases in Gas–Liquid Chromatography", F. Patte et al., p. 2239–2247, 1982.

* cited by examiner

Primary Examiner—Marc S. Hoff
Assistant Examiner—Craig Steven Miller
(74) Attorney, Agent, or Firm—Woodard, Emhardt, Moriarty, McNett & Henry LLP

(57) ABSTRACT

Disclosed is a method for taking the data generated from an array of responses from a multichannel instrument, and determining the characteristics of a chemical in the sample without the necessity of calibrating or training the instrument with known samples containing the same chemical. The characteristics determined by the method are then used to classify and identify the chemical in the sample. The method can also be used to quantify the concentration of the chemical in the sample.

63 Claims, 8 Drawing Sheets

METHODS FOR CHARACTERIZING, CLASSIFYING, AND IDENTIFYING UNKNOWNS IN SAMPLES

The present application is a Continuation-In-Part of U.S. Ser. No. 09/372,641 filed Aug. 10, 1999, now U.S. Pat. No. 6,408,250, the disclosure of which is hereby incorporated by reference.

This invention was made with Government support under Contract DE-ACO676RL01830 awarded by the U.S. Department of Energy. The Government has certain rights in the invention.

FIELD OF THE INVENTION

The present invention relates generally to a method for characterizing, classifying, and identifying unknown chemicals. Specifically, the present invention is a method for taking the data generated from an array of responses from a multichannel instrument, and determining the characteristics of a chemical in the sample without the necessity of calibrating or training the instrument with known samples containing the same chemical. The characteristics determined by the method are then used to classify and identify the chemical in the sample. The method can also be used to quantify the concentration of the chemical in the sample.

BACKGROUND OF THE INVENTION

The characterization and identification of unknown chemical is a common requirement throughout an enormous variety of scientific inquiry, running across disciplines as diverse as biochemistry and environmental science. Unsurprisingly, there exist an equally enormous variety of techniques for determining the characteristics and identity of a chemical in a sample. Liquid and gas chromatography, mass spectroscopy, absorption spectroscopy, emission spectroscopy, and chemical sensors are but a few of the myriad of techniques scientists have devised in their efforts to characterize, classify, and identify unknown chemicals in samples.

Typically, these methods rely on inferences drawn from the information that is the output of a particular instrument. For example, methods that identify chemicals through absorption spectroscopy rely on the absorption of light at certain wavelengths when the sample containing the chemical is exposed to a light. By understanding the properties of a given chemical which give rise to absorption at certain wavelengths, scientists are able to infer some of a sample's characteristics and perhaps identity the chemical(s) in the sample for example, by comparing the absorption spectra of a sample with a library of spectra taken from known chemicals. As such, these techniques often rely on determining the output signals of an instrument in response to chemicals whose identity and characteristics are known. Additionally, samples of chemicals whose concentrations are unknown may present problems for characterizing, classifying, identifying or quantifying unknowns using these types of instruments. Quantification often relies on rigorous calibration of the instrument in response to known samples of the chemical to be determined in the unknown samples. To overcome these and other difficulties, scientists have developed methods wherein a sample with an unknown chemical is interrogated with an array of channels from a particular instrument, for example, wherein the differences in the interactions between the various channels across the array with different chemicals is known from prior training and calibration on samples containing the same chemical as the unknown sample.

For example, a great many studies have described the use of arrays of chemical sensors to classify, identify, and quantify chemicals in a sample. Typically in these methods, the sensor array must be trained on samples containing chemicals of known identity and concentration in order to develop pattern recognition algorithms and calibration models that are used to classify, identify and quantify chemicals in unknown samples.[B. M. Wise, N. B. Gallagher, and M. W. A. U. S. A. Eigenvector Research, The process chemometrics approach to process monitoring and fault detection, *J. Process Control,* 6 (1996) 329–348. K. R. Beebe, R. J. Pell, and M. B. Seasholtz, *Chemometrics: A Practical Guide,* John Wiley and Sons, Inc., New York, 1998.] The only chemicals that can be classified, identified and quantified by this technique are chemicals to which the array has been previously exposed to generate output data that have been incorporated into the development of the pattern recognition algorithms and calibration models.

For example, acoustic wave sensors coated with layers of sorbent materials, such as polymers, have been investigated as array detectors by many groups.[J. W. Grate, S. J. Martin, and R. M. White, Acoustic Wave Microsensors, Part I, *Anal Chem.,* 65 (1993) 940A–948A. J. W. Grate, S. J. Martin, and R. M. White, Acoustic Wave Microsensors, Part II, *Anal. Chem.,* 65 (1993) 987A–996A. J. W. Grate, and G. C. Frye, "Acoustic Wave Sensors," in *Sensors Update,* VSH, Weinheim, 1996, pp. 37–83.] Polymer-coated acoustic wave sensors are well understood in terms of the sensors' transduction mechanisms and the interactions of analyte species with the polymeric sensing layers. A great variety of acoustic wave devices have been developed and demonstrated for chemical sensing applications in the gas and liquid phases. These include thickness shear mode (TSM) devices (also known as the quartz crystal microbalance or QCM), surface acoustic wave (SAW) devices, Leaky SAW devices, surface transverse wave (STW) devices, Love wave devices, shear-horizontal acoustic plate mode (SH-APM) devices, flexural plate wave (FPW) devices, thin film resonators, and thin rod flexural devices. Acoustic wave vapor sensors respond to any vapor that is sorbed at the sensing surface with a response that is proportional to the amount of vapor sorbed. The transduction mechanism of these sensors, which always involves a mass-loading contribution and often involves a polymer modulus change contribution, does not discriminate among sorbed species. Discrimination is dependent largely on the extent to which the applied polymer layer interacts with and sorbs particular chemical species. In addition, other sensor devices exist that are also sensitive to added mass, such as microbar, microbeam, and microcantilever devices.

The interactions between vapor molecules and polymeric sorbent phases are solubility interactions, which have been modeled and systematically investigated using linear solvation energy relationships (LSERs).[J. W. Grate, M. H. Abraham, and R. A. McGill, "Sorbent Polymer Coatings for Chemical Sensors and Arrays," in *Handbook of Biosensors: Medicine, Food, and the Environment,* CRC Press, Boca Raton, Fla., USA, 1996, pp. 593–612.]

In this approach, vapor solubility properties are characterized and quantified by solvation parameters related to polarizability, dipolarity, hydrogen bond acidity, hydrogen bond basicity, and dispersion interactions. The solvation parameters are the descriptors for vapor characteristics. LSER equations correlate the log of the partition coefficient of a vapor in a polymer with the vapor solvation parameters using a series of LSER coefficients related to the polymer solubility properties LSERs are linear multivariate correlations with solvation parameters that have been applied to many systems, including water/air partition coefficients, the sorption of vapors by blood and tissue, toxicity of gases and vapors, adsorption on solid sorbents, adsorption on fullerene, and partitioning into gas-liquid chromatographic stationary phases. In addition, LSERs have been used to correlate various sensory measures with solvation parameters, including retention across frog olfactory mucosa, respiratory tract irritation, potency, nasal pungency thresholds and odor thresholds. The partitioning of vapors into sorbent polymers at 298K has been investigated with LSERs (correlation coefficients were typically 0.99), and these LSER equations have been used to estimate the responses of polymer-coated surface acoustic wave (SAW) vapor sensors. In addition, LSERs have been developed that correlate the responses of polymer-coated SAW devices to vapor solvation parameters. These yield LSER coefficients related to partitioning and detection of vapors with polymer films on SAW device surfaces.

When a polymer-coated acoustic wave vapor sensor is exposed to a vapor, the equilibrium distribution of the vapor between the gas phase and a polymeric sorbent phase on the sensor surface is given by the partition coefficient, K. This partition coefficient is the ratio of the concentration of the vapor in the sorbent polymer, $C_S$ to the concentration of the vapor in the gas phase, $C_V$ as shown in eq. 1.

$$K = C_S/C_V \quad (1)$$

The response of a mass-sensitive acoustic wave sensor to absorption of a vapor into the polymeric sensing layer is related to the partition coefficient as shown in eq 2.

$$\Delta f_V = n \Delta f_S C_V K/\rho \quad (2)$$

The sensor's response to the mass of vapor absorbed, a frequency shift denoted by $\Delta f_V$, is dependent on the frequency shift due to the deposition of the film material onto the bare sensor (a measure of the amount of polymer on the sensor surface), $\Delta f_S$, the vapor concentration, the partition coefficient, and the density of the sorbent phase, $\rho$. If the observed response is entirely due to mass-loading, n=1. If a modulus decrease of the polymer due to vapor sorption also contributes to the frequency shift, n can be some number greater than 1, with values from 2 to 4 suggested for certain polymers. Whatever the value of n, the observed response is proportional to the amount of vapor sorbed as expressed by the partition coefficient.

The LSER method for understanding and predicting polymer/gas partition coefficients is based on eq 3, which expresses log K as a linear combination of terms that represent particular interactions.

$$\log K = c + rR_2 + s\pi_2^H + a\sum \alpha_2^H + b\sum \beta_2^H + l\log L^{16} \quad (3)$$

In this relationship, $$R_2, \pi_2^H, \sum \alpha_2^H, \sum \beta_2^H,$$

and log $L^{16}$ are solvation parameters that characterize the solubility properties of the vapor, where $R_2$ is a calculated excess molar refraction parameter that provides a quantitative indication of polarizable n and p electrons;

$$\pi_2^H$$

measures the ability of a molecule to stabilize a neighboring charge or dipole;

$$\sum \alpha_2^H$$

and $$\sum \beta_2^H$$

measure effective hydrogen-bond acidity and basicity, respectively; and log $L^{16}$ is the liquid/gas partition coefficient of the solute on hexadecane at 298K (determined by gas-liquid chromatography). The log $L^{16}$ parameter is a combined measure of exoergic dispersion interactions that increase log $L^{16}$ and the endoergic cost of creating a cavity in hexadecane leading to a decrease in log $L^{16}$. Henceforth, the parameters that describe characteristics of the sample more generally shall be referred to as "descriptors." Thus, in the case of polymer acoustic wave vapor sensors whose responses are modeled with LSERs, the descriptors are the solvation parameters $$R_2, \pi_2^H, \sum \alpha_2^H, \sum \beta_2^H,$$

and log $L^{16}$. Solvation parameters have been tabulated for some 2000 compounds The LSER equation for a particular polymer is determined by regressing measured partition coefficients for a diverse set of vapors on that polymer against the solvation parameters of the test vapors. The regression method yields the coefficients (s, r, a, b, and l) and the constant (c) in eq 3. These coefficients are related to the properties of the sorbent polymer that are complementary to the vapor properties. The necessary partition coefficients for the determination of the LSER are generally obtained by gas chromatographic measurements, but they could also be determined from the responses of a mass-sensitive acoustic wave device with a thin film of the polymer. LSER equations derived from chromatographic measurements at 298 K have been reported for fourteen sorbent polymers suitable for use on acoustic wave devices. The polymer LSER coefficients will be referred to as polymer parameters. More generally, because the polymer is the portion of this multichannel instrument that directly interacts with the chemical to produce a measured response, the term "interactive parameters" is inclusive of "polymer parameters".

In the past, sorption data for a vapor on multiple gas chromatographic stationary phases has been used in combination with "polymer parameters" describing the stationary phases to obtain values for vapor solubility parameters to be assigned to known vapors. [M. H. Abraham, G. S. Whiting, R. M. Doherty, and W. J. Shuely, Hydrogen bonding. XVI. A new solute solvation parameter, pi2H, from gas chromatographic data, *J. Chromatogr.*, 587 (1991) 213–228. F. Patte, M. Etcheto, and P. Laffort, Solubility Factors for 240 Solutes and 207 Stationary Phases in Gas-liquid Chromatography, *Anal. Chem.*, 54 (1982) 2239–2247.] The method was not used to characterize or identify unknowns, nor was a method developed to characterize an unknown at unknown concentration developed.

Despite these advances, the prevailing paradigm in the use of multichannel analytical instruments for classification and identification of components of samples is that the array must be trained to recognize the component or components of interest. In this essentially empirical approach, components that were not in the training set cannot be classified or identified. Similarly, the paradigm for using sensor arrays for vapor classification and identification is that the array must be trained to recognize the vapor or vapors of interest. In this essentially empirical approach, chemicals that were not in the training set cannot be classified or identified. For example, if a sensor array instrument is trained and calibrated on samples containing known chemicals, and then is taken to the field to detect and identify chemicals, it will only be able to identify chemicals that were in the training. If it detects a chemical that was not in the training, that chemical will either be reported as detected but unknown, or it will be misidentified as being one of the chemicals in the training. Additionally, a general purpose instrument intended to classify or identify many chemicals would have to be trained on all those chemicals, and would not be able to classify or identify other chemicals. Thus there exists a need for a method for using the data from multichannel instruments which is capable of characterizing the properties of unknown chemicals without the necessity of training the multichannel instrument on those unknown chemicals. Similarly, there exists a need to be able to transform array responses into descriptors of the chemical properties which may then be used to classify and/or identify unknown chemicals. There also exists a need for a method which allows the characterization and classification of an unknown chemical even if the concentration is unknown, and the quantification of the concentration of an unknown chemical. Finally, there exists a need for a method which allows a multichannel instrument to be trained on a finite set of chemicals and then be able to apply the instrument to characterization, classification, identification, and/or quantification of additional chemicals.

OBJECTS

Accordingly, it is an object of the present invention to provide a method for characterizing an unknown sample by obtaining a plurality of responses from a multichannel instrument, where the plurality of responses equal to or greater a plurality of descriptors, the plurality of responses is related to each of the plurality of descriptors, and the plurality of descriptors is determined from the plurality of responses.

It is a further object of the present invention to select the plurality of descriptors from the group comprising molecular interaction characteristics of the unknown sample, molecular properties of the unknown sample, molecular structural features of the sample, or combinations thereof.

It is a further object of the present invention to select the plurality of descriptors which are related to the solubility properties of the samples.

It is a further object of the present invention to select the plurality of descriptors as vapor solvation parameters.

It is a further object of the present invention to select the plurality of descriptors as parameters in a linear free energy relationship.

It is a further object of the present invention to select the plurality of descriptors as parameters in a linear salvation energy relationship.

It is a further object of the present invention to select the plurality of descriptors as descriptors in a quantitative structure activity relationship.

It is a further object of the present invention to select the plurality of descriptors as parameters in a principle components equation.

It is a further object of the present invention to model the response of each channel of a multichannel instrument with an equation including a term that is related to the plurality of descriptors.

It is a further object of the present invention to utilize a response of a multichannel instrument which is related to the thermodynamic partitioning of the unknown sample between phases.

It is a further object of the present invention to utilize a response of a multichannel instrument which is related to the partitioning of the unknown sample between the ambient environment and a plurality of sorbent phases.

It is a further object of the present invention to utilize a multichannel instrument which utilizes a plurality of gas chromatographic columns.

It is a further object of the present invention to utilize a multichannel instrument which utilizes a plurality of sensors having sorbent phases.

It is a further object of the present invention to utilize a multichannel instrument which utilizes a plurality of sensors having sorbent phases selected from the group comprising a solid surface, a self assembled monolayer, a molecular multilayer, an amorphous solid phase, a liquid, a membrane and a thin film.

It is a further object of the present invention to utilize a multichannel instrument which utilizes a stationary sorbent phase. It is a further object of the present invention to utilize a multichannel instrument which utilizes a sorbent phase as a polymer.

It is a further object of the present invention to utilize a multichannel instrument which utilizes a plurality of acoustic wave sensors selected from thickness shear mode devices, surface acoustic wave devices, Leaky surface acoustic wave devices, surface transverse wave devices, Love wave devices, shear-horizontal acoustic plate mode devices, flexural plate wave devices, thin film resonators, and thin rod flexural devices.

It is a further object of the present invention to utilize a multichannel instrument which utilizes a plurality of acoustic wave sensors coated with polymers and stationary phases.

It is a further object of the present invention to utilize a multichannel instrument which utilizes a plurality of optical sensors.

It is a further object of the present invention to utilize a multichannel instrument which utilizes a plurality of chemiresistor sensors.

It is a further object of the present invention to utilize a multichannel instrument which utilizes a plurality of chemiresitor sensors having a sorbent layer phase and a solid electronic conductor.

It is a further object of the present invention to utilize a multichannel instrument which utilizes a plurality of electrochemical or field effect transistor sensors.

It is a further object of the present invention to utilize a multichannel instrument which utilizes plurality of sensors selected from microbeam, microbar or microcantilever sensors.

It is a further object of the present invention to characterize an unknown sample, wherein the sample is modeled with a plurality of descriptors, by first obtaining a plurality of responses from a multichannel instrument, the plurality of responses equal to or greater than the plurality of descriptors, wherein the response from each channel of the multichannel instrument includes a term related to the plurality of descriptors and the term related to the plurality of descriptors contains coefficients for each descriptor; and determining the plurality of descriptors from the plurality of responses.

It is a further object of the present invention to utilize a multichannel instrument which utilizes coefficients determined from instrument responses to known compounds.

It is a further object of the present invention to utilize a multichannel instrument which utilizes coefficients determined from instrument responses to known compounds to characterize an unknown sample, wherein the sample is modeled with a plurality of descriptors, by obtaining a plurality of responses from a multichannel instrument, the plurality of responses equal to or greater than the plurality of descriptors, wherein the response from each channel of the multichannel instrument includes a term related to the plurality of descriptors, wherein the term related to the plurality of descriptors contains coefficients for each descriptor, defining a matrix P containing the coefficients, determining the plurality of descriptors from the plurality of responses and the matrix P.

It is a further object of the present invention to utilize a multichannel instrument which utilizes coefficients determined from instrument responses to known compounds to characterize an unknown sample, wherein the sample is modeled with a plurality of descriptors by obtaining a plurality of responses from a multichannel instrument, the plurality of responses equal to or greater than the plurality of descriptors, wherein the response from each channel of the multichannel instrument is included in matrix R where R is equal to $C\ 10^{(VP+1c)} M^{-1} N$, the descriptors are determined from matrix V, where V is related to a term of the form $\{\log(C^{-1} R\ M\ N^{-1})-1c\}\ P^T(PP^T)^{-1}$; C is a diagonal matrix of the concentrations of the vapors (number of vapors by number of vapors), M and N are diagonal matrices (number of channels by number of channels) of particular properties of specific channels of the detector, N (number of sensors by number of sensors, or number of polymers by number of polymers) is a diagonal matrix of the $\Delta f_S$ values of the sensors, c is a vector of constants, $P^T$ is the transpose of matrix P, $P^T(PP^T)^{-1}$ is the pseudo-inverse of P, by defining a matrix P containing the coefficients and determining the plurality of descriptors from the plurality of responses and the matrix P.

It is a further object of the present invention to utilize a multichannel instrument which utilizes coefficients determined from instrument responses to known compounds to characterize an unknown sample, wherein the sample is modeled with a plurality of descriptors, by obtaining a plurality of responses from a multichannel instrument, the plurality of responses equal to or greater than the plurality of descriptors, wherein the response from each channel of the multichannel instrument is included in matrix R where R is equal to $C\ 10^{(VP+1c)} D^{-1} F$, the descriptors are determined from matrix V, where V is equal to $\{\log(C^{-1} R\ D\ F^{-1})-1c\}\ P^T(PP^T)^{-1}$; where C is a diagonal matrix of the concentrations of the vapors (number of vapors by number of vapors), D is a diagonal matrix of the polymer densities (number of polymers by number of polymers), F is a diagonal matrix of the $\Delta f_S$ values of the sensors (number of sensors by number of sensors, or number of polymers by number of polymers), c is a vector of constants, $P^T$ is the transpose of matrix P, $P^T(PP^T)^{-1}$ is the pseudo-inverse of P, by defining a matrix P containing the coefficients, and determining the plurality of descriptors from the plurality of responses and the matrix P.

It is a further object of the present invention to utilize a multichannel instrument which utilizes coefficients determined from instrument responses to known compounds to characterize an unknown sample, wherein the sample is modeled with a plurality of descriptors, by obtaining a plurality of responses from a multichannel instrument, the plurality of responses equal to or greater than the plurality of descriptors, wherein the response from each channel of the multichannel instrument is included in matrix R where R is equal to $C\ 10^{(VP+1c)} D^{-1} F$, the descriptors are determined from matrix V, where V is equal to $\{\log(C^{-1} R\ D\ F^{-1})-1c\}\ P^T(PP^T)^{-1}$; where C is a diagonal matrix of the concentrations of the vapors (number of vapors by number of vapors), D is a diagonal matrix of the polymer densities (number of polymers by number of polymers), F is a diagonal matrix of the $\Delta f_S$ values of the sensors (number of sensors by number of sensors, or number of polymers by number of polymers), c is a vector of constants, $P^T$ is the transpose of matrix P, $P^T(PP^T)^{-1}$ is the pseudo-inverse of P, by defining a matrix P containing LSER coefficients determined from measurements of thermodynamic partitioning, and determining the plurality of descriptors from the plurality of responses and the matrix P.

It is a further object of the present invention to utilize a multichannel instrument which utilizes coefficients determined from instrument responses to known compounds to characterize an unknown sample, wherein the sample is modeled with a plurality of descriptors, by obtaining a plurality of responses from a multichannel instrument, the plurality of responses equal to or greater than the plurality of descriptors, wherein the response from each channel of the multichannel instrument is included in matrix R where R is modeled as a function of C, $S_V$, V', P', and $S_P$, where, $S_V$ contains any sample specific parameters that influence the response independent of the specific interactions of the sample with each channel, V' contains said plurality of sample parameters, P' contains parameters specific to the properties of detector channels, $S_P$ contains channel specific sensitivity parameters, and C contains sample concentration information.

It is a further object of the present invention to utilize a multichannel instrument which utilizes coefficients determined from instrument responses to known compounds to characterize an unknown sample, wherein the sample is modeled with a plurality of descriptors, by obtaining a plurality of responses from a multichannel instrument, the plurality of responses equal to or greater than the plurality of descriptors, wherein the response from each channel of the multichannel instrument is included in matrix R equal to $S_V\ C\ 10^{(V'P')}\ S_P$.

It is a further object of the present invention to utilize descriptors determined from matrix $V'_a$ equal to $\{\log(R\ S_P^{-1})\}\ P'^T_a(P'_a P'^T_a)^{-1}$ where $V'_a$ and $P'_a$ are V' and P' augmented to capture $S_V\ C$.

It is a further object of the present invention to utilize one or more of the descriptors determined according to the method of the present invention to classify an unknown sample as belonging to a class of chemicals with certain properties.

It is a further object of the present invention to utilize one or more of the descriptors determined according to the method of the present invention to classify an unknown sample as belonging to a class of chemicals with certain structural features.

It is a further object of the present invention to utilize one or more of the descriptors determined according to the method of the present invention to compare the descriptors to a table of descriptors of known chemicals to determine the identity of the unknown sample.

It is a further object of the present invention to provide a method for characterizing an unknown sample at an unknown concentration, wherein the sample is modeled with a plurality of descriptors by obtaining a plurality of responses from a multichannel instrument, the plurality of responses equal to or greater than the plurality of descriptors, wherein the response from each channel of the multichannel instrument includes a term related to the plurality of descriptors, wherein the term related to the plurality of descriptors contains coefficients for each descriptor; defining a matrix $P_a$ containing the coefficients and augmented by a vector of ones, determining the plurality of descriptors and concentration from the plurality of responses wherein the response is included in matrix R where R is equal to $10^{(V_a P_a + 1c)} D^{-1} F$; the descriptors and concentration are determined from matrix Va, where Va is equal to $\{\log(R\ D\ F^{-1}) - 1c\}\ P_a^T (P_a P_a^T)^{-1}$, $P_a$ is defined as the matrix P augmented by a vector of ones as given in $$P_a = \begin{bmatrix} P \\ 1 \end{bmatrix},$$

where P is a matrix containing the coefficients, C is a diagonal matrix of the concentrations of the vapors (number of vapors by number of vapors), D is a diagonal matrix of the polymer densities (number of polymers by number of polymers), the superscript of −1 denotes the inverse of the matrix, F is a diagonal matrix of the $\Delta f_S$ values of the sensors (number of sensors by number of sensors, or number of polymers by number of polymers), $P_a^T$ is the transpose of $P_a$, $P_a^T (P_a P_a^T)^{-1}$ is the pseudoinverse of $P_a$.

It is a further object of the present invention to provide a method for characterizing an unknown sample at an unknown concentration, wherein matrix Pa contains LSER coefficients determined from measurements of thermodynamic partitioning.

It is a further object of the present invention to provide a method for characterizing an unknown sample at an unknown concentration, wherein matrix V contains solvation parameters for vapors.

It is a further object of the present invention to provide a method for characterizing an unknown sample at an unknown concentration, wherein matrix R contains reponses of acoustic wave vapor sensors with sorbent interactor layers.

It is a further object of the present invention to provide a method for characterizing an unknown sample at an unknown concentration, wherein matrix Pa contains LSER coefficients determined from measurements of responses of acoustic wave vapor sensors to known vapors.

It is a further object of the present invention to provide a method for characterizing an unknown sample at an unknown concentration, wherein matrix V contains solvation parameters for vapors.

It is a further object of the present invention to provide a method for characterizing an unknown sample at an unknown concentration, wherein matrix R contains responses of acoustic wave vapor sensors with sorbent interactor layers.

It is a further object of the present invention to provide a method for characterizing an unknown sample at an unknown concentration, utilizing one or more of the descriptors to classify the unknown sample as belonging to a class of chemicals with certain properties.

It is a further object of the present invention to provide a method for characterizing an unknown sample at an unknown concentration, wherein the descriptors are utilized to classify the unknown sample as belonging to a class of chemicals with certain structural features.

It is a further object of the present invention to provide a method for characterizing an unknown sample at an unknown concentration, wherein the descriptors are compared to a table of descriptors of known chemicals to determine the identity of the unknown sample.

It is a further object of the present invention to provide a method for characterizing an unknown sample at an unknown concentration, wherein the sample is modeled with a plurality of descriptors by obtaining a plurality of responses from a multichannel instrument, the plurality of responses equal to or greater than the plurality of descriptors, wherein the plurality of responses is related to each of the plurality of descriptors; and determining one or more of the plurality of descriptors from the plurality of responses using the method of inverse least squares, where an individual descriptor, y, is modeled as a weighted sum of responses according to y=Xb, where X is the measured response and b is a vector of weights, generally determined by regression $b = X^+ y$ It is a further object of the present invention to provide a method for characterizing an unknown sample at an unknown concentration, wherein the regression is selected from the methods including multiple linear regression, partial least squares, and principle components regression.

It is a further object of the present invention to provide a method for characterizing an unknown sample at an unknown concentration, wherein b, the vector of weights for determination of each descriptor, is determined by a regression using responses to known compounds.

It is a further object of the present invention to provide a method for characterizing an unknown sample at an unknown concentration, wherein b, the vector of weights for determination of each descriptor, is determined by a regression using responses to known compounds to determine descriptors from the instrument response to unknowns that were not among the known compounds.

SUMMARY OF THE INVENTION

Accordingly, the present invention is a method of characterizing a component of a sample, beginning with the step of analyzing the sample with a multivariate instrument wherein each channel of the multivariate instrument gives a response that is related to various descriptors of the component.

A preferred embodiment of the present invention utilizes an array of polymer coated acoustic wave sensors as the multichannel instrument for data gathering, and is described in detail to provide an example of the practice of the present invention. The key aspect of this approach is that polymer-coated sensor responses are related to the solubility interactions between the polymer and the vapor, and the vapors' solubility properties are quantified using solvation parameters. Therefore, the response vector from a polymer-coated sensor array encodes information about vapor solubility properties, and it is therefore possible, through the method of the present invention, to transform the array data (or response vector) into vapor solvation parameters. These parameters characterize the vapor, and can be used to additionally classify or possibly identify vapors. In addition, through the method of the present invention, the array data can be transformed into vapor solvation parameters and vapor concentration simultaneously.

While the invention is described with polymer-coated acoustic wave vapor sensors as an example of the present invention, the present invention is applicable to, and broadly encompasses, the use of any such multichannel instrument as data gathering mechanisms. Thus, the present invention should be understood as a method for characterizing a component in a samples for which a "spectrum" or pattern has not been determined in advance from experimental calibrations using the multichannel instrument, regardless of which multichannel instrument is selected for the gathering of the data. Also, while the polymer-coated acoustic wave vapor sensors lend themselves to a detection method related to thermodynamic partitioning, the present invention more generally relates to the interpretation of data from any multivariate detector where the response of each channel of the detector can be modeled by a mathematical relationship (linear, non-linear or combinations thereof) correlating responses with sample descriptors. The present invention then allows descriptors of chemicals not in the training set of the particular instrument to be extracted from the instrument response. These descriptors characterize the chemical in the sample and can be used to further classify or identify the chemical.

For example, as will be apparent to one having skill in the art, there exist many other sorbent phases that are not polymers whose sorbent properties can be modeled with linear solvation energy relationships, and that could be used as sorbent phases on sensors. In addition, it is apparent that there exist other relationships and other descriptors that can be used to model sorption, partitioning, and other processes relevant to the response of a multivariate analytical instrument. It is also apparent that there exist other types of acoustic wave sensors, and types of chemical sensors other than acoustic wave sensors whose responses are dependent on the sorption of a compound onto or into a layer deposited on the surface of the sensor. For example, microbar, microbeam and microcantilever sensors also can detect the mass of a chemical sorbed into a layer. Other types of sensors that rely on partitioning of a compound into a sorbent phase include optical and chemiresistor sensors, and these sensors can be used in arrays with various sorbent layers. Another instrument that relies on sorption into multiple phases is a multicolumn gas chromatograph. Membrane inlet mass spectrometers also involve sorption of vapors into a polymeric material as a part of the process of obtaining an analytical signal. As will be apparent to one having skill in the art, the method of the present invention is readily adaptable to all such sensor systems, and the present invention should be understood to contemplate and encompass the use of all such instruments and relationships.

As used herein, the term "chemical(s)" is inclusive of elements as identified on the periodic table of the elements, compounds that are combinations of those elements, and ions that are charged elements or compounds. As used herein, the term "characteristic(s)" means physical properties, chemical properties, molecular interactions, and structural features of the sample.

In one approach of the present invention, all the relevant parameters are solved for simultaneously. It is mathematically similar to a classical least squares solution in absorbance spectroscopy, where the observed response, R, is used to obtain the concentrations C given the analyte pure component responses S. However, in the present invention the observed response, R, is used to obtain numerical values of the descriptors.

A second preferred embodiment requires solving for each descriptor (vapor parameter in the case of polymer coated acoustic wave sensors) individually. This is the inverse least squares approach, where an individual descriptor, y, is modeled as a weighted sum of the responses.

One advantage of the present invention is that it is not necessary to know the concentration of the unknown chemical in the sample independently in order to solve for the characteristics of the unknown chemical in the sample. Thus, in the preferred embodiment of the present invention utilizing polymer coated acoustic wave sensors, it is not necessary to know the vapor concentration independently in order to solve for the vapor solvation parameters. Instead, the solvation parameters and log of the concentration of an unknown vapor can be solved for simultaneously using the responses of an array of characterized sensors.

The vapor parameters that characterize a chemical in a sample can be further used to classify the chemical in the sample. For example, a vapor could be classified as a hydrogen-bond base on the basis of a postive $$\sum \beta_2^H$$

value. Alternatively, the parameter values could be used to classify a vapor as belonging to a particular compound class defined by multiple characteristics, such as a vapor that is both a hydrogen-bond base and a hydrogen bond acid. Additionally, the parameter values could be used to classify a vapor as belonging to a particular compound class, such as aliphatic hydrocarbon, aromatic hydrocarbon, or aliphatic alcohol, to name just a few.

The vapor parameters can be further used to identify the unknown chemical by comparison with a tabulation of vapor parameters for known chemicals.

Thus, the present invention represents a fundamentally different way to characterize chemical in a sample and to use that characterization to classify and possibly to identify the chemical. Additionally, it offers a fundamentally new way to quantify the concentration of a chemical from multivariate data. Provided that the multichannel instrument gives responses (multi-variate data) that can be mathematically related to sample descriptors, a chemical can be characterized even if the multi-channel instrument has never been trained on that chemical. In addition, the unknown concentration of a chemical in a sample can be estimated even if its identity is unknown and no experimental calibrations on that sample have been performed.

The subject matter of the present invention is particularly pointed out and distinctly claimed in the concluding portion of this specification. However, both the organization and method of operation, together with further advantages and objects thereof, may best be understood by reference to the following description taken in connection with accompanying drawings wherein like reference characters refer to like elements.

DETAILED DESCRIPTION OF THE INVENTION

Figure 1A:
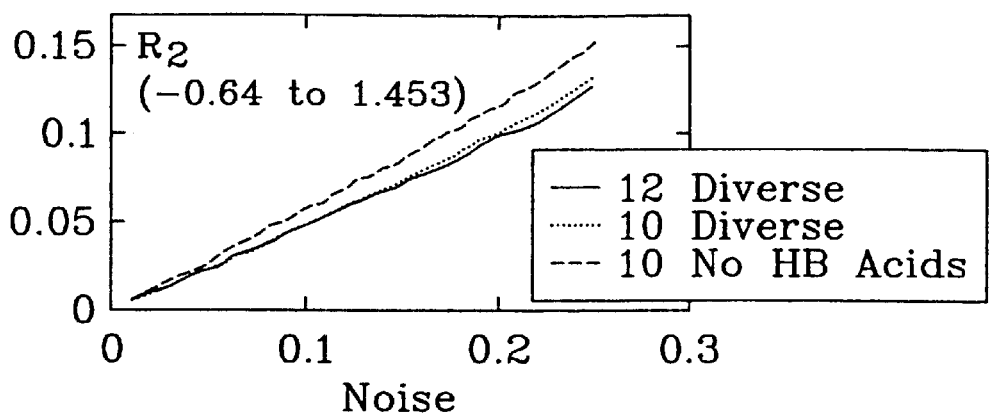
FIG. 1. Is a graph of the RMSEP for the 5 vapor LSER parameters and concentration as a function of fraction proportional noise in the response for the CLS model in experiments carried out utilizing the present invention.
Figure 1B:
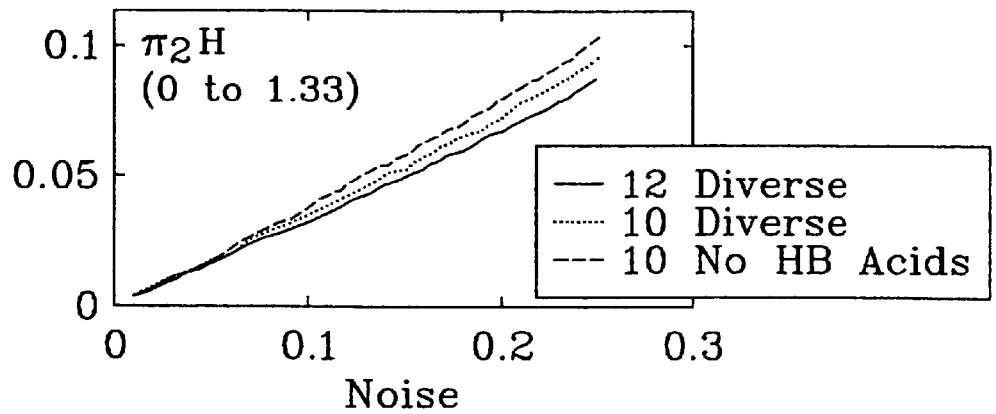
Figure 1C:
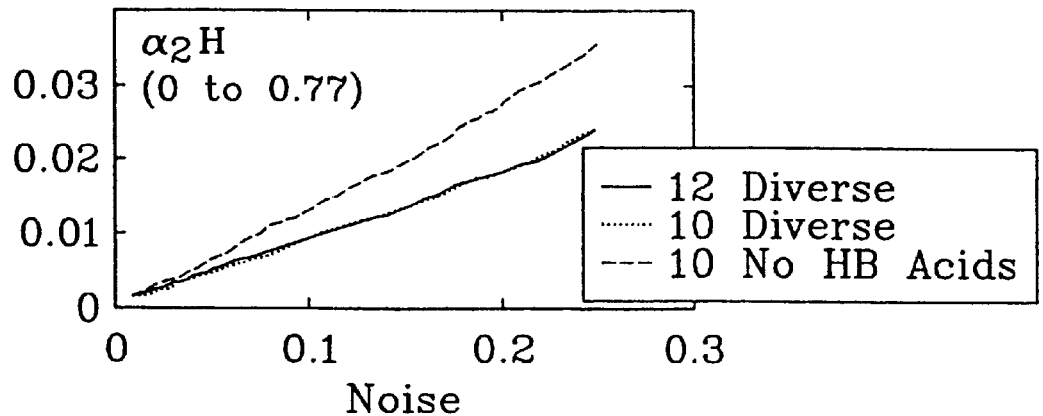
Figure 1D:
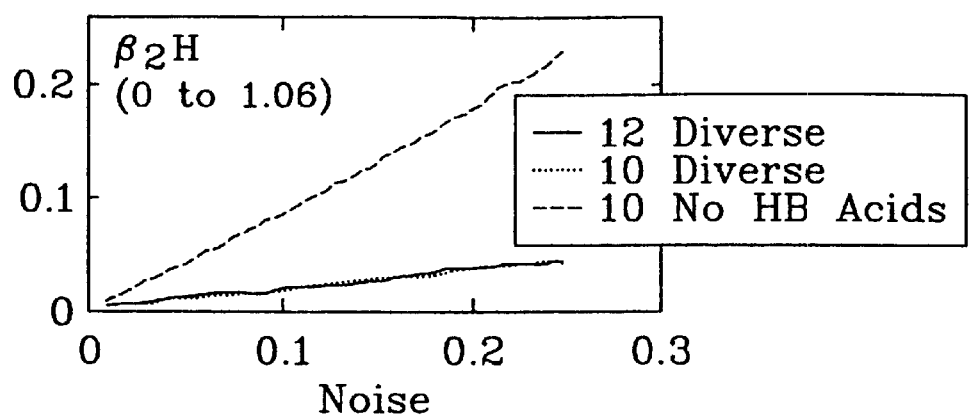
Figure 1E:
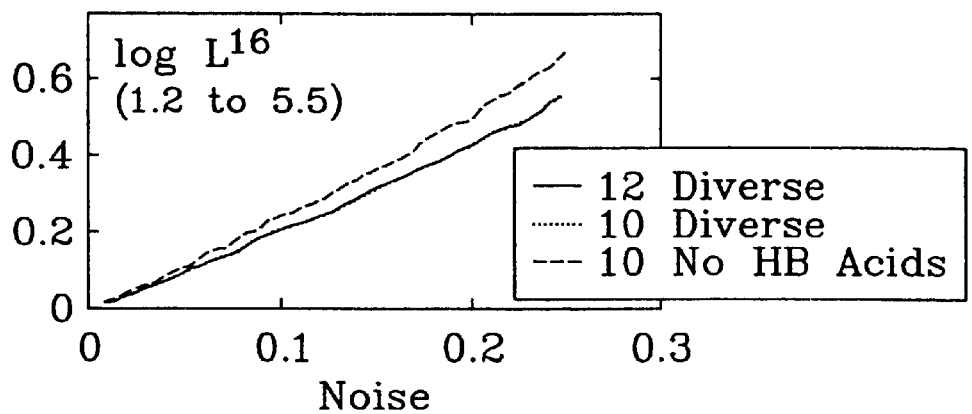
Figure 1F:
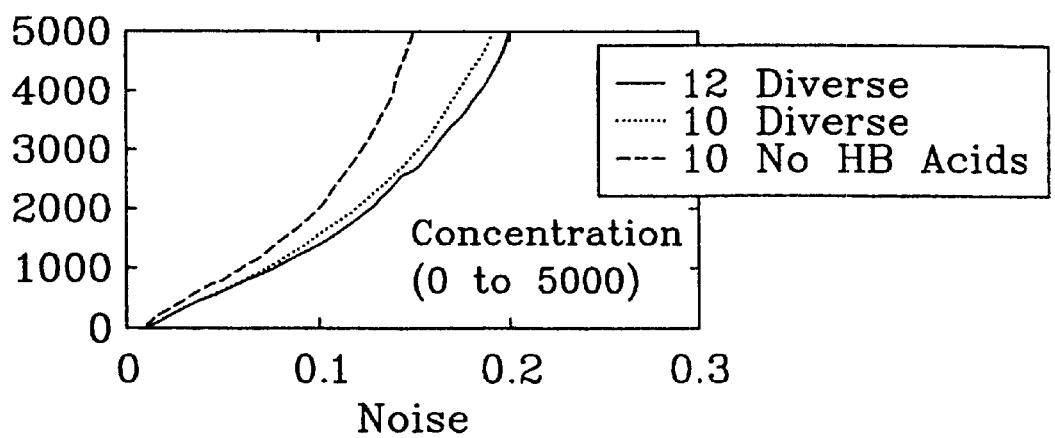

Accordingly, these and other objects of the present invention may be accomplished by first characterizing a sample using a multichannel instrument to obtain a plurality of responses, and transforming the response vector to a set of descriptors related to sample properties. One method of accomplishing this objective is mathematically analogous to classical least squares (CLS) formulations. Matrix R (samples by channels), containing the responses of the channels of the multichannel instrument, is first modeled as $$R = CS \quad (4)$$

where C is a matrix of concentrations (samples by analytes) and S is a matrix of pure component spectra (analytes by channels). If S is known, the concentrations C can be obtained given R.

$$C = R\ S^T(SS^T)^{-1} \quad (5)$$

Now consider the responses of individual channels of the multichannel instrument, where each response can be described by an equation containing a term which can in turn be estimated by some equation containing descriptors of sample components, coefficients to those descriptors, and a constant. For example, the response may be related to an equilibrium constant, K, and log K values may be estimated by a combination of terms containing descriptors of the chemical, coefficients to those descriptors, and a constant. The LSER in equation 3 can be taken as an example of such a relationship. More generally, the term in the equation for each response is related to the interaction of a component of the sample with matter or energy involved in the measurement. That interaction can be related to sample descriptors, and the instrument channels can be regarded as containing an interactor.

In matrix algebra, matrix L, containing values related to the interaction between sample components and measurement channels, can be calculated according to eq 6.

$$L = VP + 1c \quad (6)$$

Matrix V (number of samples by descriptors) contains the descriptors, and matrix P (coefficients by number of channels) contains the coefficients or parameters. The descriptors are related to a sample component and the coefficients are related to measurement channel interactors. The constants of the equations are given by the vector c (1 by number of channels), and 1 is a vector of ones (number of samples by 1).

Equation 6 can more generally be regarded as a linear relationship between a set of descriptors in V used to predict values in L, where the descriptors are weighted by coefficients in P, and the relationship contains a constant.

The responses of the channels of the multichannel detector can be related to values in L, for example, log K values, by an equation such as that in eq 7.

$$R = C\ 10^{(VP+1c)} M^{-1} N \quad (7)$$

Matrix R (samples by channels or sensors) contains the response values for particular sample/channel combinations. Matrix C (number of samples by number of samples) is a diagonal matrix of the concentrations of the samples. Matrices M and N (number of channels by number of channels) are a diagonal matrices containing constants associated with each channel of the detector. It is possible that there will be additional such diagonal matrices also describing other constants associated with each channel.. As used herein, the superscript of $-1$ denotes the inverse of the matrix.

As will be apparent to those having skill in the art, equation 7 can be regarded as a form of equation for instrument reponses in R that are related to chemical concentrations in C, the exponential of a term that uses the descriptors in a model, and additional diagonal matrices containing values related to properties of particular sensors or channels of the multichannel instrument.

Equation 7 can be rearranged to solve for V using a matrix R containing the observed responses from a multichannel instrument to various single samples. A single vector within R represents the pattern vector for a sample. The pattern vector can be used to determine the descriptors of the sample in V provided that the required properties of the instrument channels are known. The properties that are required are the coefficients or parameters in P, the constants in c, and the constants in M, N, and any additional diagonal matrices containing constants related to instrument channels. Instrument channels for which all these values are known shall be defined as 'characterized'.

Rearranging, taking the log of both sides, and then subtracting 1c from both sides of eq 7, one obtains $$\log\ (C^{-1} R\ M\ N^{-1}) - 1c = VP \quad (8)$$

To solve for the descriptors in V, it is necessary to remove the P matrix from the right side of eq 8. Since P is not a square matrix, and inverses are only defined for square matrices, one cannot simply multiply by the inverse of P. However, both sides can be multiplied by $P^T(PP^T)^{-1}$, the pseudo-inverse of P, yielding $$\{\log\ (C^{-1} R\ M\ N^{-1}) - 1c\}\ P^T(PP^T)^{-1} = V \quad (9)$$

The superscript T denotes the transpose of a matrix. It is important to note that the $PP^T$ term represents a square matrix of the same rank as P. It should be easily invertible provided that the P matrix is of full rank, i.e., the set of interactors exhibits independent variations in all interactor parameters. The $PP^T$ term must be well conditioned, and the stability of the approach requires that a diverse set of interactors is included in the array.

Eq 9 indicates that the responses of the "characterized" channels of a multichannel instrument to a test sample at a known concentration can be used to determine the descriptors of the test sample. The sample of unknown identity but known concentration is characterized in terms of its descriptors. These descriptors can be used to further classify or identify the sample.

However, in the characterization, classification, or identification of an unknown sample, the concentration would not be known. Therefore, the real question is whether the parameters for an unknown sample can be determined without the concentration, i.e. can one solve for the parameters in V without C?

To accomplish this, two new matrices are defined. The matrix $V_a$ is the matrix V augmented by the log of the sample concentrations. Thus, this matrix has a column containing log of sample concentrations in addition to the columns containing sample descriptors. In matrix algebra, $$V_a = [V \log(diag(C))] \quad (10)$$

Similarly, a matrix $P_a$ is defined as the matrix P augmented by a vector of ones of appropriate dimension (one by number of channels in the multichannel instrument). Thus, this matrix contains a row of ones at the bottom in addition to the rows of parameters. In matrix algebra, $$P_a = \begin{bmatrix} P \\ 1 \end{bmatrix} \quad (11)$$

Using these new matrices, eqs 12–14 can be derived following the approach in eqs 7–9.

$$R = 10^{(V_a P_a + 1c)} M^{-1} N \quad (12)$$

$$\log(R\, M\, N^{-1}) - 1c = V_a P_a \quad (13)$$

$$\{\log(R\, M\, N^{-1}) - 1c\} P_a^T (P_a P_a^T)^{-1} = V_a \quad (14)$$

Equation 12 is essentially the same as eq 7, except that the log of the sample concentrations has been placed in the exponential term. This is equivalent to placing the concentration in front of the exponential term as in 7, since multiplying by a constant is the same as adding to a log term. It is assumed in these equations that all the channels in the instrument give responses that are linear with concentration within the concentration range being considered. Then the difference in pattern from one concentration to another is simply a common multiplicative factor across all channels. Also, in eq 14, $P_a P_a^T$ must be invertible.

Equation 12 can be regarded as a form of equation for instrument responses in R that are related to the exponential of a term including the descriptors and the sample concentration, and additional diagonal matrices containing values related to properties of particular channels of the multichannel instrument. Furthermore, the responses of the "characterized" channels of a multichannel instrument to a test sample at an unknown concentration can be used to determine the descriptors of the test sample and the concentration of the test sample.

According to eq 14 the parameters and log of the concentration of an unknown sample can be solved for simultaneously using the responses of characterized channels of a multichannel instrument. The test sample of unknown identity and unknown concentration is characterized in terms of its descriptors. These descriptors can be used to further classify or identify the sample. In addition, the concentration of a sample can be estimated even if its identity is unknown and no experimental calibrations on that sample have been performed.

A second approach requires solving for each descriptor individually. This is the inverse least squares approach, where an individual descriptor, y, is modeled as a weighted sum of the responses $$y = Xb \quad (15)$$

where X is the measured response and b is a vector of weights, generally determined by regression:

$$b = X^+ y \quad (16)$$

where $X^+$ is the pseudoinverse of X. This pseudoinverse is defined differently depending upon the type of regression to be used. In multiple linear regression (MLR, i.e., ordinary least squares)

$$X^+ = (X^T X)^{-1} X^T \quad (17)$$

In systems where the variables in X are expected to collinear other pseudoinverses are used such as those defined by Principal Components Regression (PCR) or Partial Least Squares (PLS) regression.

In this approach, y would correspond to one of the sample parameters or concentration and X would be the (log) multichannel response. In this system, colinearity is expected any time the number of sensors in the array is greater than the number of descriptors and MLR would not be an appropriate technique for developing a model of the form in equation 15. In such cases, it is preferred that the PLS method be used.

While the general nature and operation of the present invention has been shown and described, a more in depth understanding of the invention may be acquired through a discussion of some preferred embodiments of the present invention. While the examples provided in these preferred embodiments are illustrative of the nature and operation of the present invention, those skilled in the art will recognize that the general principles demonstrated in the preferred embodiments are readily applicable in a wide variety of multichannel instruments. Accordingly, the following description of the present invention should only be regarded as illustrating the practice of the present invention, and the invention as claimed in the concluding portion of this specification should not be limited to the particular multichannel instrument described in the following preferred embodiments, but rather should be broadly construed as including other multichannel instruments.

DESCRIPTION OF THE PREFERRED EMBODIMENTS

In a preferred embodiment of the present invention, characterization of vapors using sensor array responses to obtain vapor solvation parameters is formulated in a manner analogous to classical least squares (CLS) formulations used in absorbance spectroscopy. As in the more general summary of the invention, matrix R (samples by channels), containing the responses of a spectrometer, is modeled as $$R = CS \quad (4)$$

where C is a matrix of concentrations (samples by analytes) and S is a matrix of pure component spectra (analytes by channels). If S is known, the concentrations C can be obtained given R.

$$C = R\, S^T (SS^T)^{-1} \quad (5)$$

Responses of individual polymer coated acoustic wave vapors sensors can be estimated as follows. The LSER coefficients and constants for polymers can be used in combination with tabulated vapor solvation parameters to calculate a matrix of log K values for hundreds of vapors on those polymers. These log K values can be converted to K values and then used to estimate sensor responses according to eq 2.

Calculation of log K values and sensor responses from LSERs can be reformulated in matrix algebra notation as follows. Matrix L, containing log K values, can be calculated according to eq 6.

$$L = VP + 1c \quad (6)$$

Matrix V (number of vapors by five solvation parameters) contains the vapor solvation parameters, and matrix P (5 LSER coefficients by number of polymers) contains the polymer parameters. The vapor solvation parameters are descriptors of the vapor properties. The constants of the LSER equations are given by the vector c (1 by number of polymers), and 1 is a vector of ones (number of vapors by 1).

Conversion of the predicted log K values according to eq 6 to estimated sensor responses, assuming mass-loading responses, can then be represented by eq 7.

$$R = C10^{(VP+1c)} D^{-1} F \quad (7)$$

Matrix R (vapors by polymers) contains the estimated response values as frequency shifts for particular vapor/polymer combinations. Equation 7 is similar to eq 2 (n=1), where C (number of vapors by number of vapors) is a diagonal matrix of the concentrations of the vapors, and F (number of sensors by number of sensors, or in this preferred embodiment, number of polymers by number of polymers) is a diagonal matrix of the $\Delta f_S$ values of the sensors. Similarly, D (number of polymers by number of polymers) is a diagonal matrix of the polymer densities. Again, as used herein, the superscript of −1 denotes the inverse of the matrix.

As in the more general description in the Summary of the Invention, this equation shows how the responses of the sensors of the array can be related to values in L, which are log K values in this embodiment. A single vector within R represents the pattern vector for a vapor. As practiced by this preferred embodiment of the present invention, the pattern vector can be used to determine the solvation parameters of the test vapor provided that the required properties of the sensors are known.

The properties of the sorbent films on the sensors that are required to practice this preferred embodiment of the present invention using polymer-coated acoustic wave vapors sensors are the polymer densities, the thicknesses of the films on the sensors in terms of $\Delta f_S$, and the polymer parameters, and the LSER equation constants represented in D, F, P, and c above. Sensors for which these properties are known shall be defined as 'characterized' sensors.

Again, rearranging, taking the log of both sides, and then subtracting 1c from both sides of eq 7, one obtains $$\log(C^{-1} R D F^{-1}) - 1c = VP \quad (8)$$

Again, both sides are then multiplied by $P^T(PP^T)^{-1}$, the pseudo-inverse of P, yielding $$\{\log(C^{-1} R D F^{-1}) - 1c\} P^T(PP^T)^{-1} = V \quad (9)$$

The superscript T again denotes the transpose of a matrix. It is important to note that in this preferred embodiment of the present invention, the $PP^T$ term represents a 5 by 5 square matrix of the same rank as P. It should be easily invertible provided that the P matrix is of full rank, i.e., the set of polymers exhibits independent variations in all five polymer parameters. The $PP^T$ term must be well conditioned, and the stability of the approach requires that a diverse set of polymers representing all the solubility properties of the LSER model is included in the array.

According to eq 9, the responses of an array of characterized sensors to a vapor of known concentration could be used to determine the solvation parameters of the test vapor. The test vapor of unknown identity but known concentration is characterized in terms of its salvation parameters. These characteristics can be used to further classify or identify the vapor.

As in the more general description in the Summary of the Invention, two new matrices are again defined. The matrix $V_a$ is the matrix V augmented by the log of the vapor concentrations. Thus, this matrix has a column containing log of vapor concentrations in addition to the five columns containing vapor solvation parameters. In matrix algebra, $$V_a = [V \log(\text{diag}(C))] \quad (10)$$

Similarly, a matrix $P_a$ is defined as the matrix P augmented by a vector of ones of appropriate dimension (one by number of polymers). Thus, this matrix contains a row of ones at the bottom in addition to the five rows of polymer parameters. In matrix algebra, $$P_a = \begin{bmatrix} P \\ 1 \end{bmatrix} \quad (11)$$

Using these new matrices, eqs 12–14 can be derived following the approach in eqs 7–9.

$$R = 10^{(V_a P_a + 1c)} D^{-1} F \quad (12)$$

$$\log(R D F^{-1}) - 1c = V_a P_a \quad (13)$$

$$\{\log(R D F^{-1}) - 1c\} P_a^T (P_a P_a^T)^{-1} = V_a \quad (14)$$

Equation 12 is again essentially the same as eq 7, except that the log of the vapor concentrations has been placed in the exponential term. It is again assumed in these equations that all the sensors in the array give responses that are linear with concentration within the concentration range being considered. Then the difference in pattern from one concentration to another is simply a common multiplicative factor across all sensors. Also, in eq 14, $P_a P_a^T$ must be invertible.

In this preferred embodiment 5 vapor solvation parameters are utilized, and the $P_a P_a^T$ term will be 6 by 6, which is easily invertible provided that the matrix of polymer parameters P is of full rank (5) and that none of the 5 polymer parameters are constant over all the polymers. This means the set of polymers in the array must be diverse, as previously noted in connection with eq 9.

According to eq 14 the solvation parameters and log of the concentration of an unknown vapor can be solved for simultaneously using the responses of an array of characterized sensors. The test vapor of unknown identity and unknown concentration is characterized in terms of its solvation parameters. These characteristics can be used to further classify or identify the vapor. In addition, the concentration of a vapor can be estimated even if its identity is unknown and no experimental calibrations on that vapor have been performed.

A second preferred embodiment requires solving for each vapor parameter individually. This is the inverse least squares approach, where an individual descriptor, y, is modeled as a weighted sum of the responses $$y = Xb \quad (15)$$

where X is the measured response and b is a vector of weights, generally determined by regression:

$$b = X^+ y \quad (16)$$

where $X^+$ is the pseudoinverse of X. This pseudoinverse is defined differently depending upon the type of regression to be used. In multiple linear regression (MLR, i.e., ordinary least squares)

$$X^+ = (X^T X)^{-1} X^T \tag{17}$$

In systems where the variables in X are expected to collinear other pseudoinverses are used such as those defined by Principal Components Regression (PCR) or Partial Least Squares (PLS) regression.

In this preferred embodiment utilizing polymer coated acoustic wave sensors discussed above, y would correspond to one of the vapor salvation parameters (descriptors) or concentration and X would be the (log) array response. In this system, colinearity is expected any time the number of sensors in the array is greater than the number of vapor LSER parameters and MLR would not be an appropriate technique for developing a model of the form in equation 15. In such cases, it is preferred that the PLS method be used.

In these preferred embodiments, the method described will be most effective if the ratio of polymer volume to sensor surface are is maximized and the surface is minimally adsorptive. This suggests the use of acoustic wave devices such as the QCM or FPW sensor that employ thicker polymer films (thickness in absolute terms, not in terms of frequency shift on application). A SAW device tends to use thinner films, and practical film thicknesses decrease with increasing frequency at the same time the sensitivity to adsorbed mass in increasing.

Because the acoustic wave device has some sensitivity to adsorption, and may include modulus contributions that are specific to each polymer, it may be advantageous to obtain the polymer parameters from LSERs derived from sensor response data. In this case, a calibration against many vapors of known solvation parameters would be required to obtain the required polymer parameters. Once this training was complete, the array could still be used to obtain characterization information about vapors that were not in this training set. As noted in the derivation and the experimental results, the set of polymers should be diverse.

Although derived for mass-transducing sensors above, the chemometric method for extracting descriptors from multivariate responses is very general. In a third preferred embodiment descriptors are extracted through the use of volume-transducing sensors. Sorbent polymers loaded with conductive particles can be used as chemiresistor vapor sensors where the sensors response, a change in resistance, is related to the fractional volume increase of the film on vapor sorption. Carbon-particle loaded polymers for this method of vapor sensing have been described and used for array-based sensing. The design of a chemiresistor sensor array by varying the properties of the sorbent component of a composite film was proposed by Grate in 1990 in connection with phthalocyanine/polymer composite Langmuir-Blodgett films for organic vapor sensing.[Grate, J. W.; Klusty, M.; Barger, W. R.; Snow, A. W. *Anal. Chem.* 1990, 62, 1927–1924.] The phalocyanine nanoparticles served as the current carrying component, and response characteristics were correlated with vapor sorption by the polymer component.

Recently, Severin and Lewis described detailed studies of carbon-particle loaded polymer chemiresistors that examined how vapor soption, volume increases, and sensor resistance changes are related. [Severin, E. J.; Lewis, N. S. *Anal. Chem.* 2000, 72, 2008–2015.] These authors demonstrated that sensor resistance changes are related to the extent of volume increase regardless of the identity of the vapor producing the volume increase. Correlation of the response measurements with vapor densities as liquids supported this mechanism. Therefore, just as acoustic wave sensors represent a very general method of sensing the mass of vapor sorbed, these carbon/polymer composite chemiresistor sensors represent a very general method of sensing the volume of vapor sorbed. As a result, the signals from an array of these sensors are directly related to vapor sorption, and they can be processed according to an embodiment of the present invention to obtain analyte descriptors.

The response function for a volume transducing sensor can be expressed according to eq 18.

$$R = \phi_v S \tag{18}$$

The volume fraction of the vapor in the polymer/vapor solution, $\phi_v$, times the sensitivity, S, gives the response, R. (It is assumed for the present analysis that the volume increase due to vapor sorption is small relative to the initial polymer volume, and the ratio of vapor volume to polymer volume is nearly the same as the ratio of vapor volume to the volume of the vapor/polymer solution.) The volume fraction is related to the amount of vapor in the polymer, $C_S = C_V K$. Therefore the volume fraction of vapor can be expressed according to eq 19, where $v_v$ is the specific volume of the vapor as a liquid.

$$\phi_v = v_v C_V K \tag{19}$$

Then the response function can be expressed so that the response is related to vapor specific volume and the concentration, as given in eq 20.

$$R = v_v C_V K S \tag{20}$$

The sensitivity, S, in eq 20 has a different value and different units than the sensitivity in eq 18 above, but the unchanged notation S is retained for simplicity.

It follows that the response function can be expressed in matrix algebra according to $$R = Y C \, 10^{(VP+1c)} S \tag{21}$$

The matrix Y is a diagonal matrix (number of vapors by number of vapors) containing the specific volumes of the vapors. Then the solution can be expressed as $$\{\log(Y^{-1} C^{-1} R \, S^{-1}) - 1c\} \, P^T (P P^T)^{-1} = V \tag{22}$$

This solution, like the initial solution for mass-based sensors described above, is useful when certain properties of the unknown vapor, in this case the concentration and the specific volume are known to generate the descriptors in V. In addition, matrix V can be augmented so that it contains the log of the product of the vapor concentration times the vapor specific volume. This augmented matrix will be defined as $V_b$. The P matrix is augmented with a vector of ones as before.

$$R = 10^{(V_b P_a + 1c)} S \tag{23}$$

$$\{\log(R \, S^{-1}) - 1c\} \, P_a^T (P_a P_a^T)^{-1} = V_b \tag{24a}$$

$$\{\log(r \, S^{-1}) - c\} \, P_a^T (P_a P_a^T)^{-1} = v_b \tag{24b}$$

Equation 24a expresses the solution for an entire matrix of responses, R, while equation 24b expresses the solution where a vector of descriptors $v_b$, is obtained from a single response vector, r.

This derivation shows how an array of polymer-sorption based sensors with signals proportional to volume increases can be can be used to solve for the descriptors of sorbed vapors. One also solves for the value of the log of the product of the vapor concentration times the vapor specific volume. While the latter quantity may not ordinarily be of value for classification, if the vapor were identified from the found descriptors and the specific volume determined, then the concentration could be obtained. In any case, the descriptor values can be obtained and the unknown vapor can be classified. As noted previously, the existence of this CLS type solution indicates that ILS solutions for each individual descriptor could be determined by calibration.

The product of vapor concentration in mass per volume times the vapor specific volume in volume per mass can be regarded as a vapor concentration in volume per volume units. Although this is a strange expression for concentration, regarding this product as a concentration indicates that the solution in eq 24 for a volume-based sensor array is equivalent to the solution in eq 14 for a mass-based sensor array.

Vapor specific volume is not highly correlated with the solvation parameters used as descriptors. To verify this, the liquid densities of 43 diverse compounds were tabulated with the solvation parameters and examined for correlations. The correlation matrix is given in Table 1.

TABLE 1

Correlation Matrix for Vapor Solvation Parameters and Vapor Density as a Liquid[1]

|  | $R_2$ | $H\pi_2$ | $H\Sigma\alpha_2$ | $H\Sigma\beta_2$ | $\log L^{16}$ | $d^2$ |
|---|---|---|---|---|---|---|
| $R_2$ | 1 | 0.347 | −0.264 | −0.229 | 0.576 | 0.476 |
| $H\pi_2$ | 0 | 1 | 0.020 | 0.507 | 0.277 | 0.217 |
| $H\Sigma\alpha_2$ | 0 | 0 | 1 | −0.030 | −0.428 | 0.124 |
| $H\Sigma\beta_2$ | 0 | 0 | 0 | 1 | 0.127 | −0.336 |
| $\log L^{16}$ | 0 | 0 | 0 | 0 | 1 | 0.132 |
| d | 0 | 0 | 0 | 0 | 0 | 1 |

[1]Based on a set of 43 diverse compounds.
[2]density as a liquid

As demonstrated above, the solutions embodied in equations (23) and (24) are generally valid for sensors whose signals are proportional to volume increases. It is known that the responses of carbon particle/polymer composite chemiresistor sensors, generally taken as the change in resistance relative to the initial resistance, are proportional to the relative volume change of the polymeric insulating phase. For appropriate carbon loadings, the response is linearly proportional to the vapor concentration and the fractional volume increase of the polymer. [Lonergan, M. C.; Severin, E. J.; Doleman, B. J.; Beaber, S. A.; Grubbs, R. H.; Lewis, N. S. *Chem. Mater.* 1996, 8, 2298–2312; Severin, E. J.; Doleman, B. J.; Lewis, N. S. *Anal. Chem.* 2000, 72, 658–668; Severin, E. J.; Lewis, N. S. *Anal. Chem.* 2000, 72, 2008–2015.] Given these characteristics, this sensor technology represents a volume-transducing method appropriate for a classification approach of the present invention.

In a further embodiment sorption-based sensor arrays whose individual sensors respond to both the mass and the volume of the sorbed vapor can be modeled by combining equations 7 and 21, obtaining:

$$R = C\, 10^{(VP+1c)} D^{-1} F + Y\, C 10^{(VP+1c)} S \qquad (25)$$

Rather than attempting to derive a closed form solution for vapor parameters V and Y, and concentration C given the response R and polymer parameters P, c, D, F and S, Y is taken as the identify matrix (specific volumes of the vapors as liquids=1). Under this assumption, the following solution is obtained:

$$\{\log(R(D^{+1}F+S)^{-1})-1c\}\, P_a^T(P_aP_a^T)^{-1}=V_a \qquad (26a)$$

$$\{\log(r(D^{-1}F+S)^{-1})-c\}\, P_a^T(P_aP_a^T)^{-1}=v_a \qquad (26b)$$

where $V_a$ and $P_a$ are defined as before.

Using this as an initial guess, one can determine $V_a$ and Y using direct fitting of the sensor responses to the model with, for example, a non-linear least squares optimization procedure. This has been verified on simulated data where the non-linear least squares optimization converged to the correct value.

Polymer-coated acoustic wave vapor sensors responding to both the mass of the sorbed vapor and its effect on the polymer modulus represent a combined mass and volume transducing sensor technology. [Grate, J. W. *Chemical Reviews* 2000, 100, 2627–2648; Grate, J. W.; Martin, S. J.; White, R. M. *Anal. Chem.* 1993, 65, 940A–948A; Grate, J. W.; Martin, S. J.; White, R. M. *Anal. Chem.* 1993, 65, 987A–996A.] The modulus effect can be modeled as a volume effect, since modulus changes are proportional to increases in polymer free volume. [Grate, J. W.; Klusty, M.; McGill, R. A.; Abraham, M. H.; Whiting, G.; Andonian-Haftvan, J. *Anal. Chem.* 1992, 64, 610–624; Martin, S. J.; Frye, G. C.; Senturia, S. D. *Anal. Chem.* 1994, 66, 2201-2219; Ferry, J. D. *Viscoelastic Properties of Polymers;* 3rd. Ed. ed.; John Wiley and Sons, Inc.: New York, 1980.] Models for SAW vapor sensor response expressed as the sum of mass and volume terms were reported by Grate in 1992 and 2000. [Grate, J. W.; Klusty, M.; McGill, R. A.; Abraham, M. H.; Whiting, G.; Andonian-Haftvan, J. *Anal. Chem.* 1992, 64, 610–624; Grate, J. W.; Zellers, E. T. *Anal. Chem.* 2000, 72, 2861–2868.] These assume the polymer films on the sensors are acoustically thin. The full model is given in eq 27

$$\Delta f_V = (\Delta f_S C_V K/\rho_s) + f_L(v_v C_V K)(\Delta f_S A_{SAW}/\alpha) \qquad (27)$$

The mass term is the same as the mass term above in equations 2 and 7 (where $\rho_s$ is the polymer density). The volume term includes the fractional free volume of the vapor as a liquid, $f_L$. The product $\Delta f_S\, A_{SAW}/\alpha$ gives the frequency change due to a fractional volume increase of the polymer film, where $\alpha$ is the coefficient of thermal expansion of the polymer and $A_{SAW}$ represents the kHz change in frequency due to a 1° C. change in temperature per kHz of coating on the device surface. Values for this variable are empirically measured by determining the effect of polymer thermal expansion on polymer-coated SAW device frequency. Assuming that the fractional free volume factor is a constant, the volume term can be reduced to the form in equation 20, giving $$\Delta f_V = (\Delta f_S C_V K/\rho_s) + v_v C_V K\, S \qquad (28)$$

Thus, this response model fits the form of the matrix model in eq 25.

As can be appreciated by those of skill in the art, the procedures and methods described herein are not limited to sensor arrays. In a further embodiment, there is provided a classification method for a multivariate detector where the response of each channel can be modeled with a linear relationship based on a set of sample descriptors. Unknown samples can then be characterized and classified in terms of those descriptors.

More general response models and solutions can be expressed as follows.

$$R = S_V C 10^{(V'P')} S_P \tag{29}$$

$$\{\log(R\ S_{P}{}^{-1})\} P'_a{}^T (P'_a P'_a{}^T)^{-1} V'_a \tag{30}$$

Specific interactions of the analyte with detector channel properties are modeled in the general linear relationship V'P', where V' contains analyte descriptors (not necessarily vapor analytes) and P' contains parameters specific to the properties of detector channels. The matrix $S_V$ is a diagonal matrix containing any analyte specific parameters that influence the response independent of the specific interactions of the analyte with each channel. The matrix Y in eq 21 is an example of a specific $S_V$ matrix, containing vapor specific volumes that influence sensitivity but are not part of VP, whereas in eq 7 $S_V$ is the identity matrix. The matrix $S_P$ contains channel specific sensitivity parameters, like S in eq 21 or $D^{-1}$ F in eq 7. Augmentation of V' and P' to capture $S_V C$ leads to the solution for $V'_a$ containing the analyte descriptors in V' as well as the log of the product of analyte specific sensitivity factor times the analyte concentration.

Figure 6:
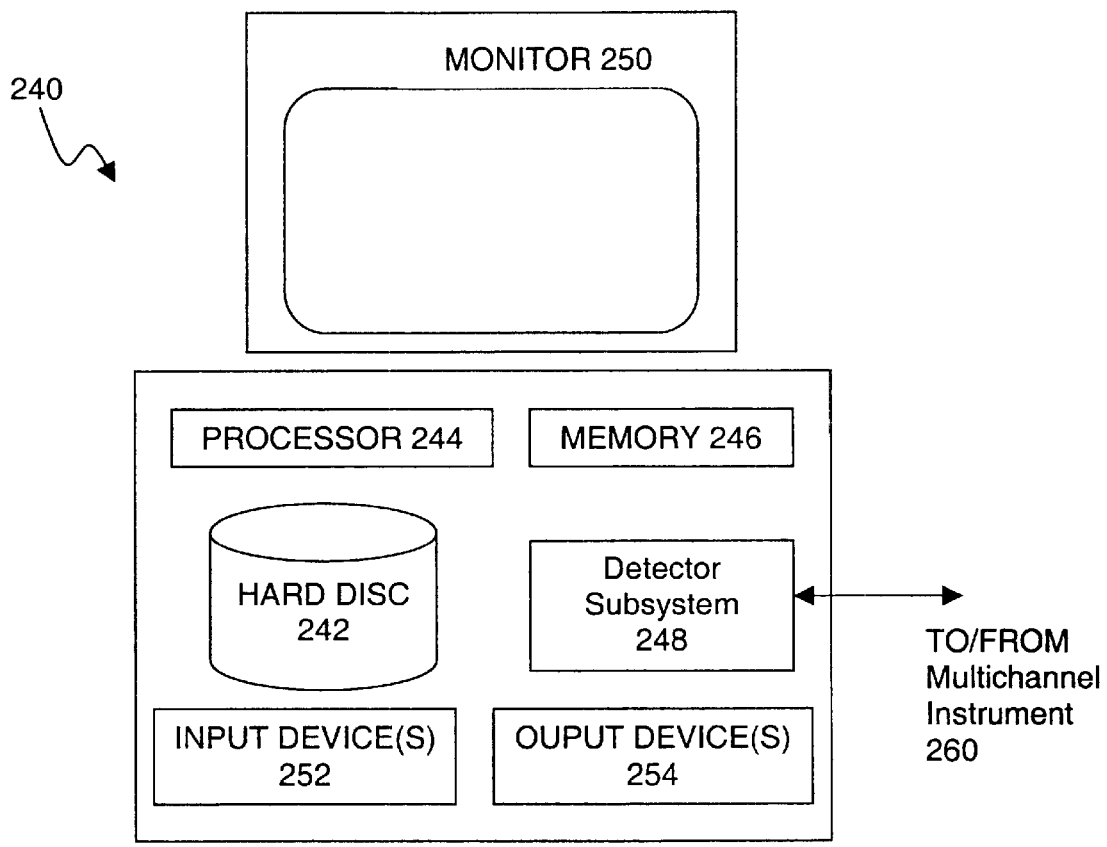
FIG. 6. Is an illustration of a system for analyzing the response from a multichannel instrument according to various embodiments of the invention.

As can be appreciated by those of skill in the art, any of the above methods can be carried out on a system such as a workstation operatively coupled to a multichannel instrument. The workstation used will now be discussed in relation to FIG. 6. In this example embodiment, the various hardware and software components that implement the above methods with respect to a response from a multichannel instrument are combined in workstation 240. Software programs and modules embodying the methods described above are encoded on hard disc 242 for execution by processor 244. Workstation 240 may include more than one processor or CPU and more than one type of memory 246, where memory 246 is representative of one or more types. Furthermore, it should be understood that while one workstation 240 is illustrated, more workstations may be utilized in alternative embodiments. Processor 244 may be comprised of one or more components configured as a single unit. Alternatively, when of a multi-component form, processor 244 may have one or more components located remotely relative to the others. One or more components of processor 244 may be of the electronic variety defining digital circuitry, analog circuitry, or both. In one embodiment, processor 244 is of a conventional, integrated circuit microprocessor arrangement, such as one or more PENTIUM II or PENTIUM III processors supplied by INTEL Corporation of 2200 Mission College Boulevard, Santa Clara, Calif., 95052, USA.

Memory 246 may include one or more types of solid-state electronic memory, magnetic memory, or optical memory, just to name a few. By way of non-limiting example, memory 246 may include solid-state electronic Random Access Memory (RAM), Sequentially Accessible Memory (SAM) (such as the First-In, First-Out (FIFO) variety or the Last-In First-Out (LIFO) variety), Programmable Read Only Memory (PROM), Electrically Programmable Read Only Memory (EPROM), or Electrically Erasable Programmable Read Only Memory (EEPROM); an optical disc memory (such as a DVD or CD ROM); a magnetically encoded hard disc, floppy disc, tape, or cartridge media; or a combination of any of these memory types. Also, memory 246 may be volatile, nonvolatile, or a hybrid combination of volatile and nonvolatile varieties.

Detector subsystem 248 provides an interface between workstation 240 and multichannel instrument 260. Monitor 250 provides visual output from workstation 250 to an operator. Additional input device(s) 252 and output device (s) 254 provide interfaces with other computing and/or human entities. Further, detector subsystem 248 and workstation 240 may include additional and/or alternative components as would occur to one skilled in the art.

EXAMPLE 1

A series of experiments were undertaken to demonstrate the utility of the present invention as practiced in the preferred embodiments. A matrix of predicted log K values was calculated beginning with a table of salvation parameters for 280 vapors. The parameters were taken from published tabulations [M. H. Abraham, J. Andonian-Haftvan, G. Whiting, A. Leo, and R. W. Taft, Hydrogen Bonding. Part 34. The factors that influence the solubility of gases and vapours in water at 298 K, and a new method for its determination, *J. Chem. Soc., Perkin Trans.* 2, (1994) 1777–1791. M. H. Abraham, Scales of hydrogen-bonding: Their construction and application to physicochemical and biochemical processes, *Chemical Society Reviews*, 22 (1993) 73–83.]

Vapors included alkanes(24), cycloalkanes (11), alkenes (including dienes and cycloalkenes) (18), terminal linear alkynes (7), fluoroalkanes (2), chloroalkanes (21), bromoalkanes (10), iodoalkanes (7), ethers (8), aldehydes (11), ketones (12), esters (15), nitrites (8), amines (12), nitroalkanes (7), dimethylamides (2), alkanoic acids (6), alcohols (14), fluoroalcohols (3), thiols (7), sulfides (3), organophosphorus compounds (2), aromatic hydrocarbons (11), chlorobenzenes (4), bromo- and iodobenzenes (6), various aromatic compounds with oxygen-containing functional groups (7), various aromatic compounds with N-containing functional groups (4), phenols (22), and pyridines (11). The solvation parameter ranges represented by these vapors were: parameter, range; $R_2$, 0.64 to 1.453; $\pi_2^H$, 0 to 1.33; $\sum \alpha_2^H$, 0 to 0.77; $\sum \beta_2^H$, 0 to 1.06; and log $L^{16}$, 1.2 to 5.5. LSERs and densities for a diverse set of twelve polymers were taken from previous papers. [J. W. Grate, S. J. Patrash, and M. H. Abraham, Method for estimating polymer-coated acoustic wave vapor sensor responses, *Anal. Chem.*, 67 (1995) 2162–2169. M. H. Abraham, J. Andonian-Haftvan, C. M. Du, V. Diart, G. Whiting, J. W. Grate, and R. A. McGill, Hydrogen Bonding. XXIX. The characterisation of fourteen sorbent coatings for chemical microsensors using a new solvation equation, *J. Chem. Soc., Perkin Trans.* 2, (1995) 369–378.] These polymers are listed in Table 2.

TABLE 2

POLYMERS

| Abbreviation | Description | Properties |
| --- | --- | --- |
| PIB | poly(isobutylene) | nonpolar aliphatic hydrocarbon material |
| PECH | poly(epichlorohydrin) | slightly basic ether linkages and slightly dipolar chloromethyl groups |
| OV25 | an OV stationary phase | polarizable phenyl groups |
| OV202 | an OV stationary phase | dipolar nonbasic trifluoropropyl groups |
| PVPR | poly(vinyl proprionate) | moderately basic esters |
| PVTD | poly(vinyl tetradecanal) | acetal and residual alcohol groups |
| PEM | poly(ethylene maleate) | dipolar basic ester linkages |
| SXCN | an OV stationary phase | dipolar basic cyanopropyl groups |
| PEI | poly(ethylenimine) | basic amine linkages |
| SXPYR | a polysiloxane | basic dipolar aminopyridyl groups |
| FPOL | fluoropolyol | strong hydrogen bond acid |
| SXFA | a polysiloxane | strong hydrogen bond acid |

The matrix of log K values was converted to a matrix of estimated sensor responses, assuming mass-loading responses, 250 kHz of material on each sensor, and a concentration of 5000 mg/m³ for each vapor. This produced a matrix of estimated responses, R, for use in modeling studies.

For some purposes, this matrix was divided into a training set with 195 vapors and a prediction set containing 85 vapors. Vapors from each of the various compound classes were distributed proportionately between the training and prediction sets. In addition each vapor was labeled with a compound class chosen from the list above.

After setting up the original matrices for V, P, L, and R in an Excel spreadsheet, all further calculations were performed in MATLAB Version 5.2 (The MathWorks, Natick Mass.) with PLS_Toolbox 2.0 (Eigenvector Research, Manson, Wash.).

A matrix R (12 by 280) containing vapor sensor responses $\Delta f_V$ was calculated as described above, where V (5 by 280) contained solvation parameters for 280 diverse vapors, P (12 by 5) contained polymer parameters for 12 diverse polymers, and vector c (1 by 12) contained the constants for those polymers. This matrix was used as the basis for modeling studies to investigate approaches for determining vapor parameters from sensor array responses. Two subsets of the 12 polymer set were also examined in some experiments. Removal of FPOL and SXFA from the 12 polymer set yielded a 10 polymer set lacking a strong hydrogen bond acid polymer. Thus, this represents a less diverse polymer set. Removal of PVPR and PVTD from the 12 polymer set yielded a 10 polymer set that preserved chemical diversity in the array.

Initial calculations were carried out with all vapors at 5000 mg/m³ concentration. Given characterized sensors (i.e., D, F, P, and c known), the vapor parameters, V, can be calculated from R to machine accuracy. This is simply a rearrangement of the original calculations to obtain R. Then matrix R was modified so that the vapors were at random concentrations between 0 and 5000 mg/m. Given characterized sensors, it was verified that $V_a$ could be calculated from R, obtaining the vapor parameters and the vapor concentrations correctly to machine accuracy. Plots of predicted parameters and concentrations against the actual parameters and concentrations are perfectly linear with slopes of one.

These calculations began with essentially perfect noiseless data. The effect of measurement noise on the determination of vapor parameters and concentration was investigated by adding noise to the sensor responses in R. The added measurement noise was proportional to the response and was normally distributed. The noise was added independently across the polymers.

Vapor parameters and concentrations were calculated by solving for $V_a$ and the errors in these results were determined as a function of the added measurement noise. The root-mean-square errors of prediction (RMSEP) for each of the parameters and the concentration are plotted versus fraction noise in the data (e.g. 0.1 indicates that the standard deviation of the noise was 10% of the sensor signal) in FIG. 1. Each line on the plot corresponds to a different set of polymers. The solid line includes the 12 polymers in Table 1. With the exception of concentration, the errors grow approximately linearly with noise, as would be expected. Concentration errors grow approximately exponentially with noise. This is a result of the fact that the log of the concentration is predicted, and it must be transformed. The results for a set of ten diverse polymers are similar to those for the twelve polymer set, but ten polymer array lacking hydrogen-bond acid polymers gives poorer results, especially for the $$\sum \beta_2^H$$

parameter (as might be expected).

The errors in the original solvation parameter scales can be taken as about 0.03 units for the $$\pi_2^H, \sum \alpha_2^H,$$

and $$\sum \beta_2^H$$

parameters. The error for the log $L^{16}$ parameter can be taken as 0.1 units or less. These parameters are all related to free energies and were determined from experimental data on partitioning or complexation equilibria. The $R_2$ parameters is different, since it is calculated from molar refraction values for liquids, and extended by a group contribution scheme. The parameter errors in FIG. 1 for $$\pi_2^H, \sum \alpha_2^H,$$

and $$\sum \beta_2^H$$

are approximately 0.06, 0.02, and 0.03, respectively, for 20% noise in the sensor responses. This is comparable to the error in the original parameters. The log $L^{16}$ error at 20% sensor noise is somewhat larger at 0.3–0.4 log units.

Figure 2:
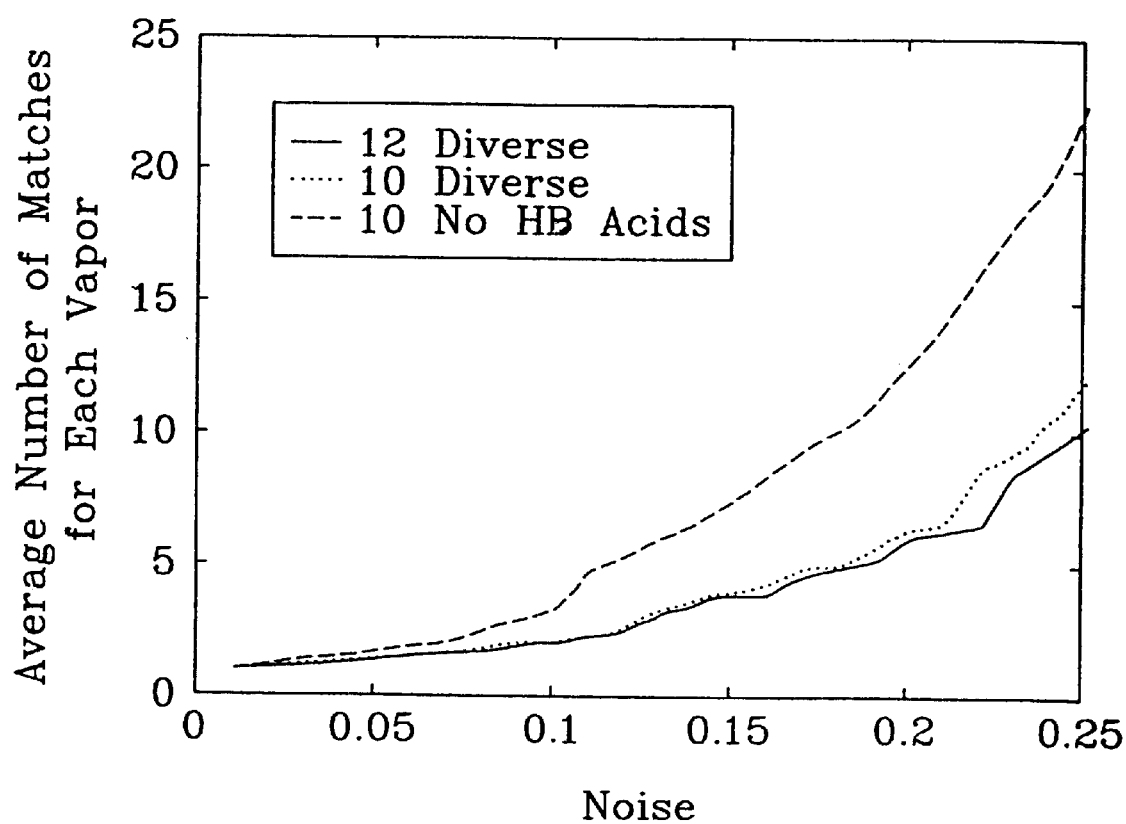
FIG. 2. Is a graph showing the average number of vapors within salvation parameter error bound of two times the standard error as a function of the noise in the frequency shift response of the array in experiments carried out utilizing the present invention. The lower trace (solid line) represents the analysis using all 12 polymers, a diverse set. The upper trace (short dashes) represents the results using a 10 polymer set lacking strongly hydrogen bond acidic polymers fluoropolyol and SXFA. The middle trace (long dashes) was created using a diverse set of 10 polymers (PVPR and PVTD left out).

Once sensor responses in R have been used to solve for $V_a$, the found solvation parameters can be matched to tabulated solvation parameters for known vapors. The effect of measurement noise on this matching process for vapor identification was examined. Given the prediction error information just described, it is reasonable to construct error bounds of two times the RMSEP around each of the vapor parameters for each vapor in $V_a$. This is equivalent to a two standard deviation bound around the predictions. For each vapor, it is possible to determine how many other vapors in $V_a$ fit within this bound. The optimal answer is one, where the only vapor that fits within the error bound is the correct one. As the noise increases and the error bounds increase, more vapors will fit. The results of this analysis are shown in the lowest trace in FIG. 2, plotting the average number of matches for each vapor as a function of the added measurement noise. Here we are considering the lower (solid) line on the plot for all 12 polymers. For noise levels up to about 10%, typically two or fewer vapors are within the error bound, suggesting the ability to identify the correct vapor will be pretty good up to this noise level. Above this, the number of vapors within the error bounds tends to grow more rapidly. Nevertheless, even at 20% noise, the number of vapors fitting the solvation parameters within error bounds is still limited (ca. 5 or 6). It is worth noting that this is a conservative evaluation of identification "precision", since independently derived limits define a larger space than a group determination of the error bounds.

Figure 3:
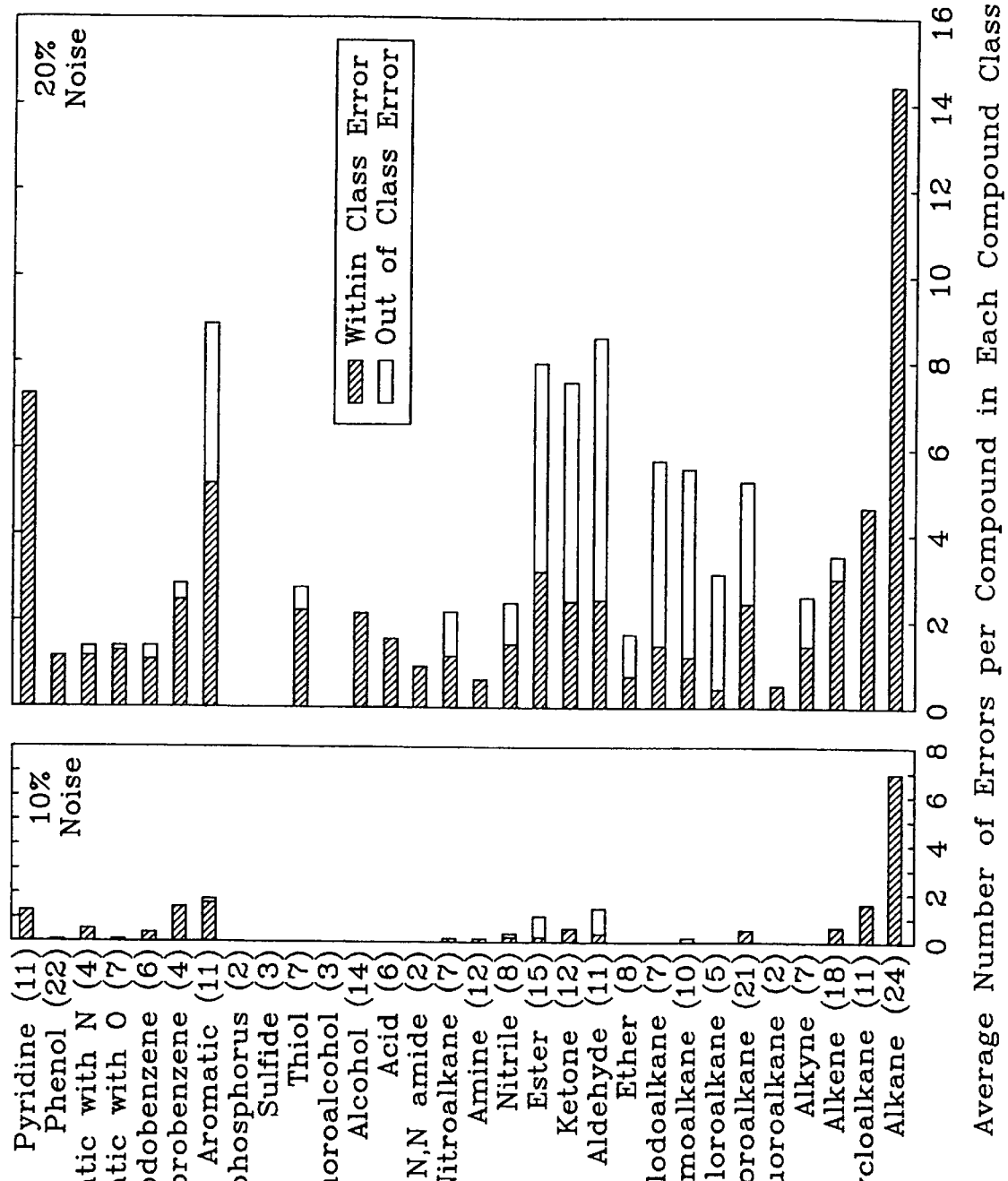
FIG. 3. Is a graph of the average number of extra matching vapors within solvation parameter error bound of two times the standard error according to compound classes, showing in-class and out-of-class errors in experiments carried out utilizing the present invention. Results are shown for 10% and 20% noise levels in the frequency shift response of the array.
Figure 4A:
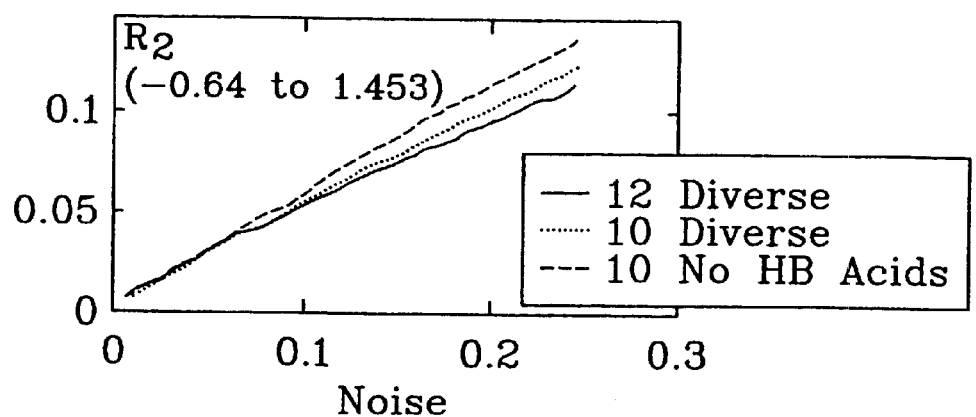
FIG. 4. Is a graph of the RMSEP for the 5 vapor LSER parameters and concentration as a function of fraction proportional noise in the response for the ILS models in experiments carried out utilizing the present invention.
Figure 4B:
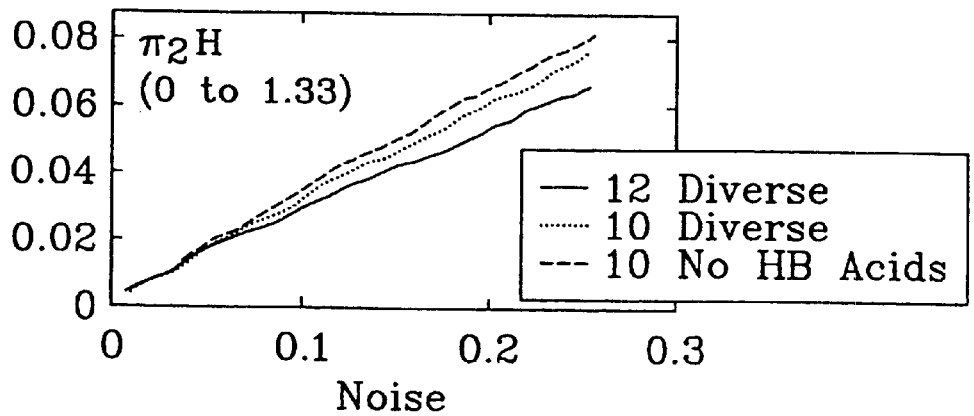
Figure 4C:
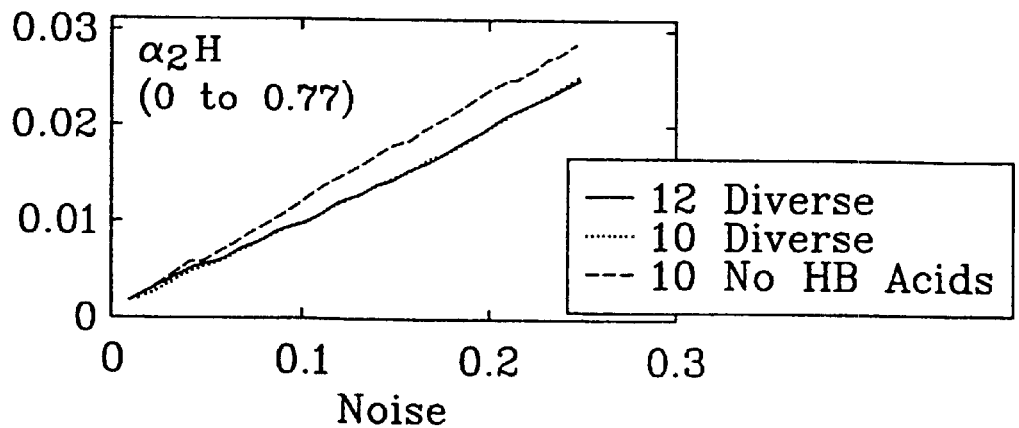
Figure 4D:
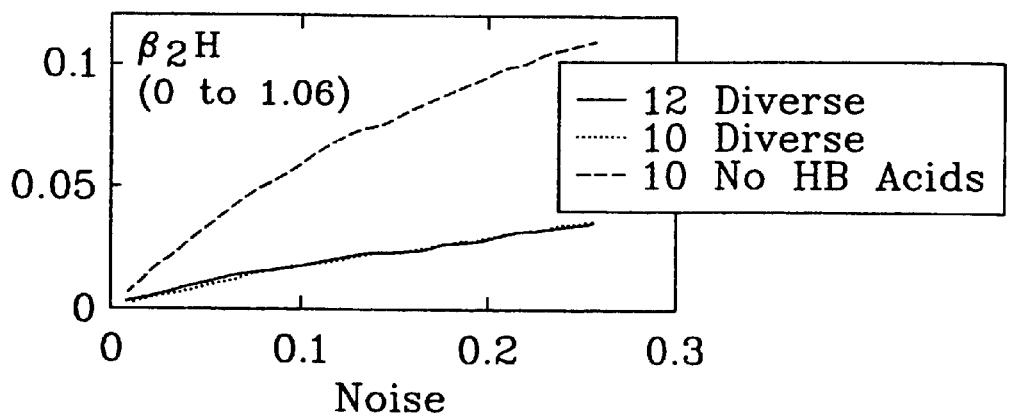
Figure 4E:
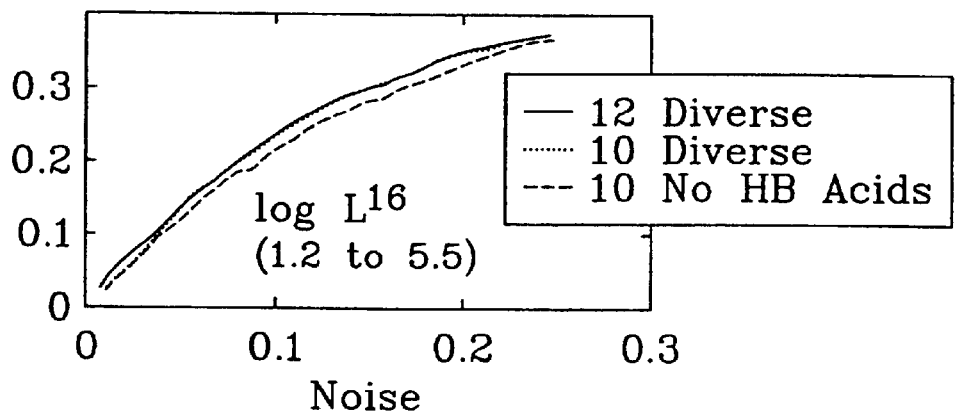
Figure 4F:
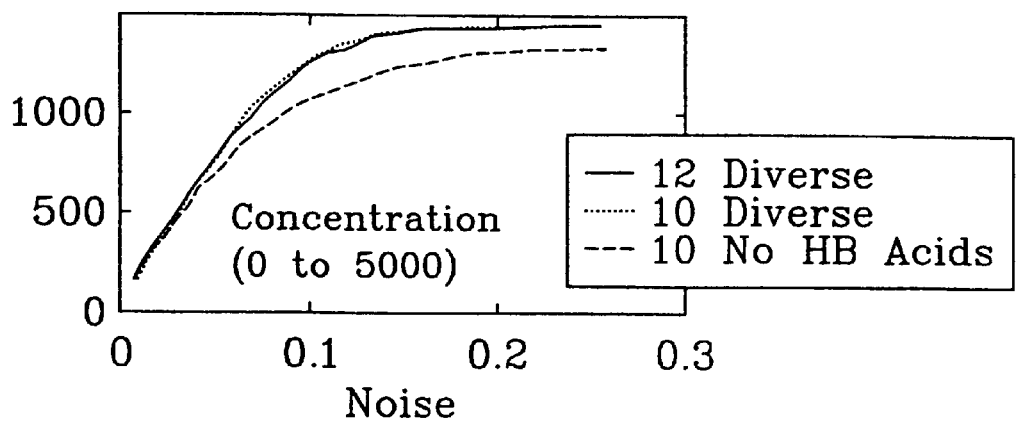
Figure 5:
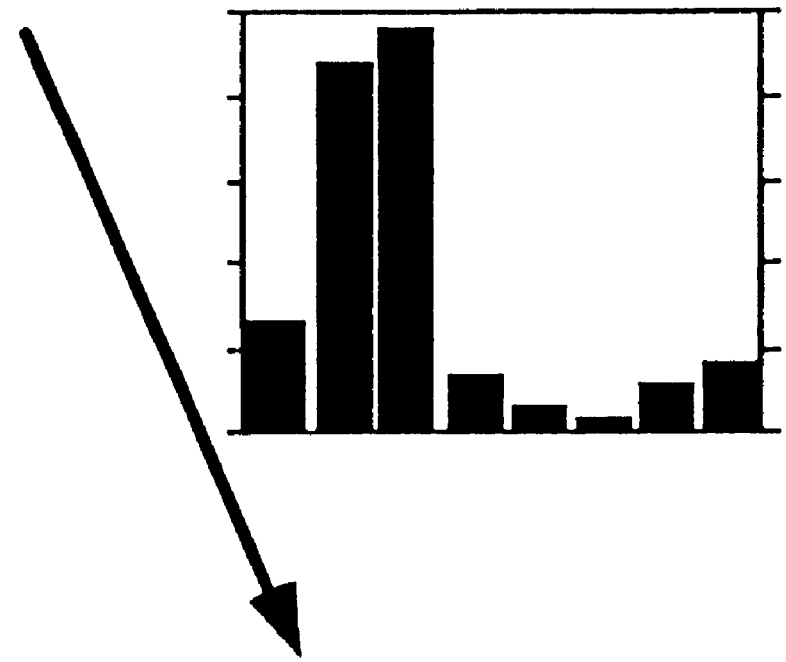
FIG. 5. Is an illustration of the method of converting an array response vector, shown as a bar graph, into descriptors of the detected vapor, where the descriptors are the solvation parameters from a linear solvation energy relationship for vapor sorption.

Vapors within some compound classes tend to have larger numbers of vapors fitting within the error bounds for each vapor than those in other compound classes. For example, there is an average of fifteen vapors, all alkanes, fitting within the error bounds for each alkane at the 20% noise level. This result is due to the fact that alkanes are distinguished from one another only by their log $L^{16}$ values (i.e., they are very similar to one another), the data set contains many alkanes, and many isomers are included. For all other vapor classes the results are much better, and the results averaged over all vapors, shown in FIG. 2, are skewed to higher values by the poorer results for alkanes. The plots in FIG. 3 show the average number of vapors fitting within the error bounds with the correct vapor for each compound class, based on modeling with all 12 polymers. Henceforth, a compound fitting within the error bounds for another compound shall be defined as an error. In-class errors and out-of-class errors are indicated. The results are quite good at 10% noise and a diverse set of polymers. Except for ethers and ketones, most errors are within class. At 20% noise, out-of-class errors increase somewhat, especially for ethers, ketones, and aldehydes, all vapors with basic oxygen containing functional groups.

Because the derivation for this analysis approach indicates that a diverse set of polymers is required, the accuracy of vapor identification was also examined using a less diverse polymer set. The two hydrogen bond acidic polymers were removed and the results with this 10 polymer set were determined, as shown in FIG. 2. Because these hydrogen bond acidic polymers are not commercially available, this set represents the type of less diverse array that will most likely occur. As seen in the graph, vapor classification is not too bad at measurement noise of 5% or less, but it becomes significantly degraded relative to a diverse array at measurement noise above 10%. To demonstrate that this effect is related to diversity rather than polymer number, the same analysis was done with a ten sensor array that included the hydrogen bond acidic polymers. This array gives results similar to those of the diverse 12 sensor array (see FIG. 2). The array lacking hydrogen-bond acids yielded more out-of-class errors than the diverse arrays, as found by examining plots (not shown) similar to those in FIG. 3. At 10% noise, overall results are not bad, but out-of-class errors are notable for esters, ethers, ketones, and aldehydes. At 20% noise, there are large numbers of out-of-class errors in most compound classes.

The reason for the effect of polymer diversity on the prediction error is suggested by the form of eq 12. Note the $(P_a P_a^T)^{-1}$ in the equation. If the matrix $P_a P_a^T$ is ill-conditioned, the problem will be subject to considerable numerical instability. Small changes in the response due to noise will result in large changes in the predictions, an undesirable effect. The amount of ill-conditioning present can be assessed by calculating the condition number of the matrix. The condition number is the ratio of the largest to smallest singular value of the matrix. When all 12 polymers are considered, the condition of $P_a P_a^T$ is 5947. When the hydrogen bond acid polymers are removed, the condition number jumps to 9562. This increase in the condition number is, in part, responsible for the increase in prediction errors. The condition number of the $P_a P_a^T$ matrix was calculated when leaving out PVPR and PVTD was 5998. Thus, leaving out these polymers had little effect on the condition of the matrix.

Overall, these results demonstrate the concept that a sensor array consisting of characterized sensors is able to characterize an unknown vapor in terms of its solvation parameters and match it to a limited number of vapor candidates. The technique can also provide an estimate of the unknown concentration. The concentration estimation, however, is much more sensitive to the measurement noise. The derivation for this approach assumes that patterns are constant regardless of vapor concentration, i.e., sensor calibration curves are linear. The tolerance for noise in solving for vapor parameters and matching to known vapors suggests that the method may also tolerate moderate nonlinearity in sensor calibration curves.

EXAMPLE 2

Modeling was also carried out using ILS methods to determine models for each individual vapor parameter from sensor responses as given in eq 15 for the vapors in Example 1. In this approach, the sensor response data can be empirically used without knowing the polymer parameters. In other words, one need not have characterized sensors as described above. The matrix of sensor responses to particular vapors in V was divided into training and prediction sets. Models were developed using PLS with six latent variables, training on R and C to get V.

PLS models developed for each vapor solvation parameters with the sensor responses in the training set were able to predict the parameters for the vapors in the prediction set to machine accuracy. However, this test was based on perfect data. The effect of measurement noise was investigated by adding noise to both the training set and the prediction set. PLS models were developed using the training set data with noise added. Then the ability to predict the vapor parameters of the vapors in the prediction set using the "noise-added" response data was tested.

The results are shown in FIG. 4. These results are very similar to those for the CLS models shown in FIG. 2. In fact, the ILS models perform modestly better than the CLS models. Thus, it appears reasonable that one could train on sensor responses to develop models to predict vapor solvation parameters even if the polymer parameters are not known. These models could then be used to classify unknowns that were not in the training.

We claim:

1. A method of characterizing an unknown sample comprising:
   obtaining a plurality of responses from a multi channel instrument,
   modeling each of said plurality of responses as a function of a plurality of descriptors, and
   determining said plurality of descriptors from said plurality of responses,
   wherein said plurality of responses is equal to or greater than said plurality of descriptors and,
   wherein said sample is modeled with said plurality of descriptors.

2. The method of claim 1 wherein:
   said responses are modeled as a function of C, $S_V$, V', P', and $S_P$ where,
   $S_V$ contains any sample specific parameters that influence the response independent of the specific interactions of the sample with each channel
   V' contains said plurality of descriptors,
   P' contains parameters specific to the properties of detector channels,
   $S_P$ contains channel specific sensitivity parameters, and
   C contains sample concentration information.

3. The method of claim 2 wherein:
   said responses are included in matrix R equal to $S_V$ C $Z^{(VP)}$ $S_P$, where Z is a scalar.

4. The method of claim 3 wherein:
   said plurality of sample parameters are determined from $V'_a$ equal to $\{\log z(R\ S_p^{-1})\}P'_a{}^T(P'_a P'_a{}^T)^{-1}$ where;
   $V'_a$ is V' augmented to contain the log z of the products of the sample specific sensitivity factors and the concentration, and $P'_a$ is P' augmented with a vector of ones,
   The superscripts of $^{-1}$ and $^T$ denote the inverse and transpose of the matrix respectively.

5. The method of claim 4 wherein $S_V$ and C are diagonal matrices.

6. The method of claim 5 wherein the sample is a vapor.

7. The method of claim 2 wherein said multi channel instrument includes a plurality of diverse sensors that output a signal that depends on the amount of said sample that interacts with said sensor.

8. The method of claim 7 wherein said amount is selected from the group consisting of mass, volume, and mass plus volume.

9. The method of claim 8 wherein the amount is a volume and $S_V$ is a diagonal matrix with sample specific volumes.

10. The method of claim 8 wherein the amount is a mass and $S_V$ is the identity matrix.

11. A method for characterizing an unknown sample comprising:
    determining a plurality of descriptors used to model the sample by modeling a plurality of responses obtained from a multichannel instrument as a function of each of the plurality of descriptors wherein the number of responses is greater than the number of descriptors.

12. The method of claim 11 wherein said plurality of descriptors are molecular interaction characteristics of said unknown sample, molecular properties of said unknown sample, molecular structural features of said sample, or combinations thereof.

13. The method of claim 11 wherein said plurality of descriptors are related to a plurality of solubility properties of said samples.

14. The method of claim 11 wherein said plurality of descriptors are vapor solvation parameters.

15. The method of claim 11 wherein said plurality of descriptors are parameters in a linear free energy relationship.

16. The method of claim 11 wherein said plurality of descriptors are parameters in a linear solvation energy relationship.

17. The method of claim 11 wherein said plurality of descriptors are descriptors in a quantitative structure activity relationship.

18. The method of claim 11 wherein said plurality of descriptors are parameters in a principle components equation.

19. The method of claim 11 wherein the response of each channel of said multichannel instrument is modeled by an equation including a term that is related to said plurality of descriptors.

20. The method of claim 11 wherein the plurality of responses of said multichannel instrument are related to the thermodynamic partitioning of said unknown sample between phases.

21. The method of claim 11 wherein the plurality of responses of said multichannel instrument are related to the partitioning of said unknown sample between the ambient environment and a plurality of sorbent phases.

22. The method of claim 11 wherein said multichannel instrument utilizes a plurality of gas chromatographic columns.

23. The method of claim 11 wherein said multichannel instrument utilizes a plurality of sensors having sorbent phases.

24. The method of claim 23 wherein the sorbent phase is selected from the group comprising a solid surface, a self assembled monolayer, a molecular multilayer, an amorphous solid phase, a liquid, a membrane and a thin film.

25. The method of claim 11 wherein the sorbent phase is a stationary sorbent phase.

26. The method of claim 23 wherein the sorbent phase is a polymer.

27. The method of claim 23 wherein said multichannel instrument utilizes a plurality of acoustic wave sensors selected from the group of thickness shear mode devices, surface acoustic wave devices, Leaky surface acoustic wave devices, surface transverse wave devices, Love wave devices, shear-horizontal acoustic plate mode devices, flexural plate wave devices, thin film resonators, and thin rod flexural devices.

28. The method of claim 11 wherein said multichannel instrument utilizes a plurality of acoustic wave sensors coated with polymers and stationary phases.

29. The method of claim 11 wherein said multichannel instrument utilizes a plurality of optical Sensors.

30. The method of claim 11 wherein said multichannel instrument utilizes a plurality of chemiresistor sensors.

31. The method of claim 11 wherein said multichannel instrument utilizes a plurality of chemiresitor sensors having a sorbent layer phase and a solid electronic conductor.

32. The method of claim 11 wherein said multichannel instrument utilizes a plurality of sensors selected from the group of electrochemical and field effect transistor sensors.

33. The method of claim 11 wherein said multichannel instrument utilizes a plurality of sensors selected from the group of microbeam, microbar and microcantilever sensors.

34. The method of claim 11 wherein said multichannel instrument includes a plurality of diverse sensors that output a signal that depends on the amount of said sample that interacts with said sensor.

35. The method of claim 34 wherein said amount is mass, volume, or mass plus volume.

36. Computer-readable media tangibly embodying a program of instructions executable by a Computer to perform the method of claim 11.

37. The method of claim 11 further comprising utilizing one or more of said descriptors to classify said unknown sample as belonging to a class of chemicals with certain properties.

38. The method of claim 11 further comprising utilizing one or more of said descriptors to classify said unknown sample as belonging to a class of chemicals with certain structural features.

39. The method of claim 11 further comprising comparing said descriptors to a table of descriptors of known chemicals to determine the identity of said unknown sample.

40. The method of claim 11 wherein said responses are modeled as a function of C, $S_V$, V', P', and $S_P$, where, $S_V$ contains any sample specific parameters that influence the response independent of the specific interactions of the sample with each channel V' contains said plurality of descriptors, P' contains parameters specific to the properties of detector channels, $S_P$ contains channel specific Sensitivity parameters, and C contains sample concentration information.

41. The method of claim 40 wherein said responses are included in matrix R equal to $S_V \, C \, Z^{(V'P')} \, S_P$, where Z is a scalar.

42. The method for characterizing un unknown sample comprising:

determining a plurality of descriptors used to model the sample from a plurality of responses obtained from a multichannel installment wherein the number of responses is at least equal to the number of descriptors and wherein the plurality of responses are mathematically modeled with coefficients for each descriptor.

43. The method of claim 42 wherein said coefficients are coefficients in a linear free energy relationship.

44. The method of claim 42 wherein said coefficients are coefficients in a linear solvation energy relationship.

45. The method of claim 42 wherein said coefficients are coefficients in a quantitative structure activity relationship.

46. The method of claim 42 wherein said coefficients are coefficients in a principle components equation.

47. The method of claim 42 wherein said coefficients are coefficients in a linear free energy relationship related to sorbent phase properties.

48. The method of claim 42 wherein said coefficients are coefficients in a linear free energy relationship based on thermodynamic partition coefficients.

49. The method of claim 42 wherein said coefficients are determined from instrument responses to known compounds.

50. Computer-readable media tangibly a program of instructions executable by a computer to perform the method of claim 42.

51. The method of claim 42 further comprising utilizing one or more of said descriptors to classify said unknown sample as belonging to a class of chemicals with certain properties.

52. The method of claim 42 further comprising utilizing one or more of said descriptors to classify said unknown sample as belonging to a class of chemicals with certain structural features.

53. The method of claim 42 further comprising comparing said descriptors to a table of descriptors of known chemicals to determine the identity of said unknown sample.

54. The method of claim 42 wherein said responses are modeled as a function of C, $S_V$, V', P', and $S_P$ where, $S_V$ contains any sample specific parameters that influence the response independent of the specific interactions of the sample with each channel V' contains said plurality of descriptors, P' contains parameters specific to the properties of detector channels, $S_P$ contains channel specific sensitivity parameters, and C contains sample concentration in formation.

55. The method of claim 54 wherein said responses are included in matrix R equal to $S_V \, C \, Z^{(V'P')} \, S_P$, where Z is a scalar.

56. A method for characterizing an unknown sample comprising:

defining a matrix P containing coefficients for a plurality of descriptors used to model the sample; and determining said plurality of descriptors from said matrix P and a plurality of responses obtained from a multichannel instrument wherein the number of responses is at least equal to the number of descriptors and wherein the plurality of responses are a function of the coefficients.

57. The method of claim 56 wherein matrix P contains LSER coefficients determined from measurements of thermodynamic partitioning.

58. The method of claim 56 wherein said plurality of descriptors are determined from said matrix P, said plurality of responses, and a matrix V containing solvation parameters for vapors.

59. The method of claim 56 wherein said plurality of descriptors are determined from said matrix P, said plurality of responses, and a matrix R containing responses of acoustic wave vapor sensors with sorbent interactor layers and wherein said matrix P contains LSER coefficients determined from measurements of responses of acoustic wave vapor sensors to known vapors.

60. The method of claim 56 further comprising the step of utilizing one or more of said descriptors to classify said unknown sample as belonging to a class of chemicals with certain properties.

61. The method of claim 56 further comprising the step of utilizing one or more of said descriptors to classify said unknown sample as belonging to a class of chemicals with certain structural features.

62. The method of claim 56 further comprising the stop of comparing said descriptors to a table of descriptors of known chemicals to determine the identity of said unknown sample.

63. Computer-readable media tangibly embodying a program of instructions executable by a computer to perform the method of claim 56.

* * * * *